(12) United States Patent
Inubushi et al.

(10) Patent No.: US 8,741,030 B2
(45) Date of Patent: Jun. 3, 2014

(54) METAL COMPLEX, AND ADSORBENT, OCCLUSION MATERIAL AND SEPARATOR MATERIAL MADE FROM SAME

(75) Inventors: Yasutaka Inubushi, Kurashiki (JP); Chikako Ikeda, Kurashiki (JP); Koichi Kanehira, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 133 days.

(21) Appl. No.: 13/578,262

(22) PCT Filed: Feb. 24, 2011

(86) PCT No.: PCT/JP2011/054200
§ 371 (c)(1),
(2), (4) Date: Aug. 10, 2012

(87) PCT Pub. No.: WO2011/105521
PCT Pub. Date: Sep. 1, 2011

(65) Prior Publication Data
US 2012/0312164 A1 Dec. 13, 2012

(30) Foreign Application Priority Data
Feb. 24, 2010 (JP) ................................. 2010-038329

(51) Int. Cl.
*C07D 213/22* (2006.01)
*B01J 20/22* (2006.01)
*C07C 51/41* (2006.01)
*C07C 7/12* (2006.01)
*C07D 213/53* (2006.01)
*B01D 53/02* (2006.01)

(52) U.S. Cl.
CPC ............... *B01J 20/226* (2013.01); *C07C 51/41* (2013.01); *C07C 7/12* (2013.01); *C07D 213/22* (2013.01); *C07D 213/53* (2013.01); *B01D 53/02* (2013.01); *B01D 2253/204* (2013.01); *B01D 2257/50* (2013.01); *B01D 2257/702* (2013.01); *Y10S 95/90* (2013.01)
USPC ....... 95/116; 95/141; 95/900; 546/2; 502/401

(58) Field of Classification Search
CPC ...... C07C 51/41; C07C 51/412; C07C 65/21; C07C 7/12; B01D 53/02; B01D 2253/204; B01D 2257/102; B01D 2257/104; B01D 2257/108; B01D 2257/11; B01D 2257/302; B01D 2257/304; B01D 2257/404; B01D 2257/406; B01D 2257/50; B01D 2257/702; B01J 20/226; B01J 20/3425; B01J 20/3483; B01J 20/3491; C07D 213/226; C07D 213/53; C07D 401/14

USPC .................. 95/116, 117, 127–130, 135, 136, 95/138–141, 143; 546/2; 502/401
See application file for complete search history.

(56) References Cited

U.S. PATENT DOCUMENTS 7,141,313 B2 * 11/2006 Seo .............................. 428/690
8,415,493 B2 * 4/2013 Eddaoudi et al. ............. 556/132
(Continued)

FOREIGN PATENT DOCUMENTS

JP 2000 109485 4/2000
JP 2001 131178 5/2001
(Continued)

OTHER PUBLICATIONS

Uemura, K., et al., "Expected Materials for the Future," vol. 2, No. 12, pp. 44 to 51, (2002).
(Continued)

*Primary Examiner* — Frank Lawrence, Jr.
(74) *Attorney, Agent, or Firm* — Oblon, Spivak, McClelland, Maier & Neustadt, L.L.P.

(57) ABSTRACT

This invention provides a metal complex having a gas adsorption capability, a gas storing capability, and a gas separation capability. The present invention attained the above object by a metal complex comprising:
a dicarboxylic acid compound (I) represented by the following General Formula (I),

[Chem. 1]

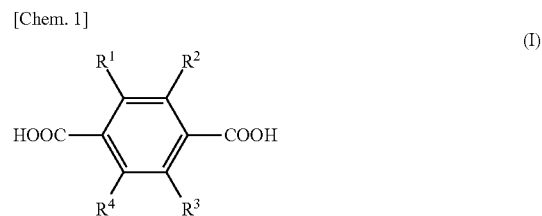

(I)

wherein $R^1$, $R^2$, $R^3$, and $R^4$ are as defined in the specification;
at least one metal ion selected from ions of a metal belonging to Group 2 and Groups 7 to 12 of the periodic table; and
an organic ligand capable of bidentate binding to the metal ion, the organic ligand belonging to the $D_{\infty h}$ point group, having a longitudinal length of not less than 8.0 Å and less than 16.0 Å, and having 2 to 7 heteroatoms.

20 Claims, 23 Drawing Sheets

(56) References Cited

U.S. PATENT DOCUMENTS

| | | | |
|---|---|---|---|
| 2008/0177098 A1* | 7/2008 | Bahnmuller et al. | 556/118 |
| 2011/0237796 A1 | 9/2011 | Inubushi et al. | |
| 2012/0247561 A1* | 10/2012 | Chi et al. | 136/263 |
| 2013/0139686 A1* | 6/2013 | Wilmer et al. | 95/127 |

FOREIGN PATENT DOCUMENTS

| | | |
|---|---|---|
| JP | 2001 348361 | 12/2001 |
| JP | 2003 275531 | 9/2003 |
| JP | 2003 278997 | 10/2003 |
| JP | 2003 342260 | 12/2003 |
| JP | 2004 74026 | 3/2004 |
| JP | 2004 161675 | 6/2004 |
| JP | 2005 232033 | 9/2005 |
| JP | 2005 232034 | 9/2005 |
| JP | 2005 232222 | 9/2005 |
| JP | 2008 247884 | 10/2008 |
| WO | 2009 098001 | 8/2009 |
| WO | 2010 021345 | 2/2010 |

OTHER PUBLICATIONS

Matsuda, R., et al., "PETROTECH" vol. 26, pp. 97 to 104, (2003).
International Search Report Issued Mar. 29, 2011 in PCT/JP11/054200 Filed Feb. 24, 2011.

* cited by examiner

METAL COMPLEX, AND ADSORBENT, OCCLUSION MATERIAL AND SEPARATOR MATERIAL MADE FROM SAME

TECHNICAL FIELD

The present invention relates to a metal complex and a production method thereof, as well as an adsorbent material, a storage material, and a separation material composed of the metal complex. More specifically, the present invention relates to a metal complex composed of a specific dicarboxylic acid compound, at least one metal ion, and an organic ligand capable of bidentate binding to the metal ion. The metal complex of the present invention is suitable for an adsorbent material, a storage material, or a separation material for adsorbing, storing, or separating carbon dioxide, hydrogen, carbon monoxide, oxygen, nitrogen, hydrocarbons having from 1 to 4 carbon atoms, noble gases, hydrogen sulfide, ammonia, water vapor, organic vapor, and the like.

BACKGROUND ART

In the fields of deodorization, exhaust gas treatment, and the like, various adsorbent materials have so far been developed. Activated carbon is a representative examples of these, and it has been used widely in various industries for the purpose of air cleaning, desulfurization, denitrification, or removal of harmful substances by making use of its excellent adsorption performance. In recent years, demand for nitrogen has been increasing, for example, in the semiconductor manufacturing process and the like. Such nitrogen is produced from air by using molecular sieving carbon according to the pressure swing adsorption process or temperature swing adsorption process. Molecular sieving carbon is also used for separation and purification of various gases such as purification of hydrogen from a cracked methanol gas.

When a mixture of gases is separated according to the pressure swing adsorption process or temperature swing adsorption process, it is the common practice to separate it based on the difference between the gases in equilibrium adsorption amount or rate of adsorption to molecular sieving carbon or zeolite used as a separation adsorbent material. When the mixture of gases is separated based on the difference in equilibrium adsorption amount, conventional adsorbent materials cannot selectively adsorb thereto only the gas to be removed, and the separation coefficient decreases, making it inevitable that the size of the apparatus used therefor increases. When the mixture of gases is separated into individual gases based on the difference in rate of adsorption, on the other hand, only the gas to be removed can be adsorbed, although it depends on the kind of gas. It is necessary, however, to alternately carry out adsorption and desorption, and also in this case, the apparatus used therefor should be larger.

On the other hand, there has also been developed, as an adsorbent material providing superior adsorption performance, a polymer metal complex undergoing a change in dynamic structure when exposed to external stimulation (see Non-patent Documents 1 and 2). When this novel polymer metal complex undergoing a change in dynamic structure is used as a gas adsorbent material, it does not adsorb a gas until a predetermined pressure but it starts gas adsorption at a pressure exceeding the predetermined pressure. In addition, a phenomenon is observed in which the adsorption starting pressure differs depending on the nature of the gas.

Application of these phenomena to adsorbent materials used in a gas separation apparatus employing a pressure swing adsorption system enables very efficient gas separation. It can also decrease the pressure swing width, contributing to energy savings. Further, it can contribute to size reduction of the gas separation apparatus, making it possible to increase competitiveness in terms of costs when a high-purity gas is put on the market as a product. Moreover, even if the high-purity gas is used in a company's own plant, the costs paid for the equipment requiring a high-purity gas can be reduced, resulting in a reduction of manufacturing costs of the final product.

Known examples of using a polymer metal complex undergoing a change in dynamic structure as a storage material or a separation material are (1) a metal complex having an interdigitated framework (see Patent Documents 1 and 2), (2) a metal complex having a two-dimensional square-grid framework (see Patent Documents 3, 4, 5, 6, 7, and 8), and (3) a metal complex having an interpenetrated framework (see Patent Document 9).

At present, however, further reducing the apparatus size is desired for cost reduction. To this end, further improving the separation performance is desired.

Patent Document 9 discloses a polymer metal complex composed of a terephthalic acid, a metal ion, and 4,4'-bipyridyl. However, Patent Document 9 is completely silent about the effect conducive to separation performance provided by an organic ligand capable of bidentate binding.

Further, Patent Document 10 discloses a polymer metal complex composed of a terephthalic acid derivative, a metal ion, and an organic ligand capable of bidentate binding to the metal ion. However, Patent Document 10 only discloses, in Examples, a polymer metal complex composed of a terephthalic acid, a copper ion, and pyrazine, and it is completely silent about the effect conducive to the mixed gas separation performance provided by an organic ligand capable of bidentate binding.

Further, Patent Document 11 discloses a polymer metal complex composed of a terephthalic acid derivative, a metal ion, and an organic ligand capable of bidentate binding to the metal ion. However, Patent Document 11 only discloses, in Examples, a polymer metal complex composed of a terephthalic acid, a copper ion, and 1,4-diazabicyclo[2.2.2]octane, and it is completely silent about the effect conducive to the mixed gas separation performance provided by an organic ligand capable of bidentate binding.

Citation List

Patent Document
[Patent Document 1] Japanese Unexamined Patent Application Publication No. 2004-161675
[Patent Document 2] Japanese Unexamined Patent Application Publication No. 2008-247884
[Patent Document 3] Japanese Unexamined Patent Application Publication No. 2003-275531
[Patent Document 4] Japanese Unexamined Patent Application Publication No. 2003-278997
[Patent Document 5] Japanese Unexamined Patent Application Publication No. 2005-232222
[Patent Document 6] Japanese Unexamined Patent Application Publication No. 2004-74026
[Patent Document 7] Japanese Unexamined Patent Application Publication No. 2005-232033
[Patent Document 8] Japanese Unexamined Patent Application Publication No. 2005-232034
[Patent Document 9] Japanese Unexamined Patent Application Publication No. 2003-342260
[Patent Document 10] Japanese Unexamined Patent Application Publication No. 2000-109485

[Patent Document 11] Japanese Unexamined Patent Application Publication No. 2001-348361

Non-Patent Documents

[Non-patent Document 1] Kazuhiro Uemura and Susumu Kigatawa, "Expected Materials for the Future", 2, 44 to 51 (2002)

[Non-patent Document 2] Ryotaro Matsuda and Susumu Kitagawa, "PETROTECH", 26, 97 to 104 (2003)

SUMMARY OF INVENTION

Technical Problem

Accordingly, an object of the invention is to provide a metal complex that can be used as a gas adsorbent material having a high effective adsorption amount, a gas storage material having a high effective storage amount, and a gas separation material ensuring a superior performance in mixed gas separation.

Solution to Problem

As a result of intensive study, the present inventors found that the above object can be achieved by a metal complex composed of a specific dicarboxylic acid compound, at least one metal ion, and an organic ligand capable of bidentate binding to the metal ion, leading to the completion of the present invention.

Specifically, the present invention provides the following.

(1) A metal complex comprising:

a dicarboxylic acid compound (I) represented by the following General Formula (I),

[Chem. 1]

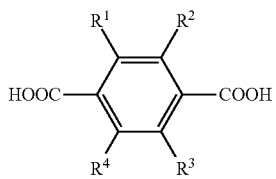

(I)

wherein $R^1$, $R^2$, $R^3$, and $R^4$ are the same or different, and each independently represents a hydrogen atom, an alkyl group that may have a substituent, an alkoxy group, a formyl group, an acyloxy group, an alkoxycarbonyl group, a nitro group, a cyano group, an amino group, a monoalkyl amino group, a dialkyl amino group, a acylamino group or a halogen atom; or $R^1$ and $R^2$, or $R^3$ and $R^4$ may be taken together to form an alkylene group or an alkenylene group that may have a substituent;

at least one metal ion selected from ions of a metal belonging to Group 2 and Groups 7 to 12 of the periodic table; and an organic ligand capable of bidentate binding to the metal ion, the organic ligand belonging to the $D_{\infty h}$ point group, having a longitudinal length of not less than 8.0 Å and less than 16.0 Å, and having 2 to 7 heteroatoms.

(2) The metal complex according to (1), wherein the dicarboxylic acid compound is at least one member selected from terephthalic acid (benzene-1,4-dicarboxylic acid), 2-methoxyterephthalic acid, and 2-nitroterephthalic acid.

(3) The metal complex according to (1), wherein the organic ligand capable of bidentate binding is at least one member selected from 1,2-bis(4-pyridyl)ethyne, 1,4-bis(4-pyridyl)benzene, 3,6-di(4-pyridyl)-1,2,4,5-tetrazine, and 4,4'-bis(4-pyridyl)biphenyl.

(4) The metal complex according to any one of (1) to (3), wherein the metal ion is a zinc ion.

(5) An adsorbent material comprising the metal complex of any one of (1) to (4).

(6) The adsorbent material according to (5), wherein the adsorbent material is for adsorbing carbon dioxide, hydrogen, carbon monoxide, oxygen, nitrogen, hydrocarbons having 1 to 4 carbon atoms, noble gases, hydrogen sulfide, ammonia, sulfur oxides, nitrogen oxides, siloxanes, water vapor, or organic vapor.

(7) A storage material comprising the metal complex of any one of (1) to (4).

(8) The storage material according to (7), wherein the storage material is for storing carbon dioxide, hydrogen, carbon monoxide, oxygen, nitrogen, hydrocarbons having 1 to 4 carbon atoms, noble gases, hydrogen sulfide, ammonia, water vapor, or organic vapor.

(9) A separation material comprising the metal complex of any one of (1) to (4).

(10) The separation material according to (9), wherein the separation material is for separating carbon dioxide, hydrogen, carbon monoxide, oxygen, nitrogen, hydrocarbons having 1 to 4 carbon atoms, noble gases, hydrogen sulfide, ammonia, sulfur oxides, nitrogen oxides, siloxanes, water vapor, or organic vapor.

(11) The separation material according to (9), wherein the separation material is for separating carbon dioxide and methane, carbon dioxide and hydrogen, carbon dioxide and nitrogen, ethane and methane, or methane and air.

(12) A method for producing the metal complex according to claim 1, comprising reacting, in a solvent, a dicarboxylic acid compound (I), at least one metal salt selected from salts of a metal belonging to Group 2 and Groups 7 to 12 of the periodic table, and an organic ligand capable of bidentate binding to the metal ion, thereby precipitating a metal complex, the organic ligand belonging to the $D_{\infty h}$ point group, having a longitudinal length of not less than 8.0 Å and less than 16.0 Å, and having 2 to 7 heteroatoms.

Advantageous Effects of Invention

The present invention provides a metal complex composed of a specific dicarboxylic acid compound, at least one metal ion, and an organic ligand capable of bidentate binding to the metal ion.

Due to its superior adsorption performance with respect to various gases, the metal complex of the present invention can be used as an adsorbent material for adsorbing carbon dioxide, hydrogen, carbon monoxide, oxygen, nitrogen, hydrocarbons having from 1 to 4 carbon atoms, noble gases, hydrogen sulfide, ammonia, sulfur oxides, nitrogen oxides, siloxanes, water vapor, organic vapor, and the like.

Further, due to its superior storage performance with respect to various gases, the metal complex of the present invention can also be used as a storage material for storing carbon dioxide, hydrogen, carbon monoxide, oxygen, nitrogen, hydrocarbons having from 1 to 4 carbon atoms, noble gases, hydrogen sulfide, ammonia, water vapor, organic vapor, and the like.

Furthermore, due to its superior separation performance with respect to various gases, the metal complex of the present invention can further be used as a separation material for separating carbon dioxide, carbon monoxide, oxygen, nitrogen, hydrocarbons having from 1 to 4 carbon atoms, noble gases, hydrogen sulfide, ammonia, sulfur oxides, nitrogen oxides, siloxanes, water vapor, organic vapor, and the like.

Figure 1:
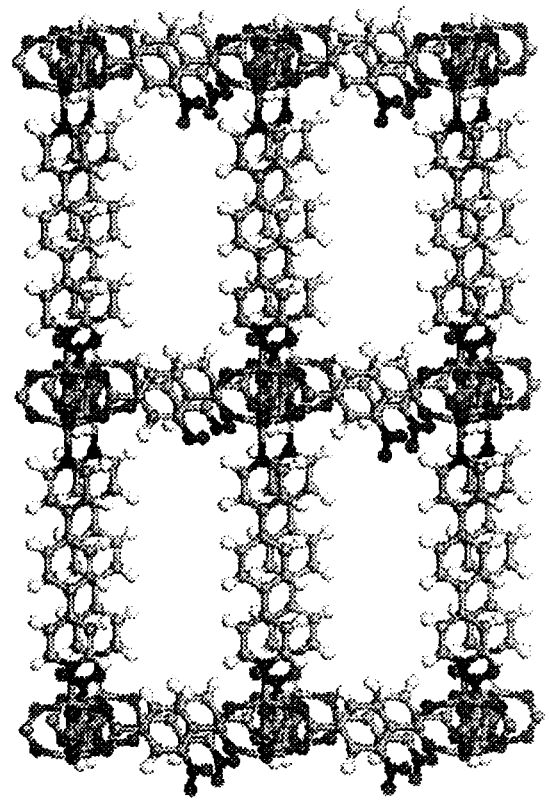
[FIG. 1] A schematic diagram illustrating a jungle-gym-type framework in which an organic ligand capable of bidentate binding is coordinated to the axial position of a metal ion in a paddle-wheel-type framework composed of a metal ion and a carboxylate ion of the dicarboxylic acid compound (I).

In the measurement results of a powder X-ray diffraction pattern, the horizontal axis represents a diffraction angle (2θ) and the vertical axis represents a diffraction intensity expressed by cps (counts per second).

In the measurement results of an adsorption/desorption isotherm, the horizontal axis represents an equilibrium pressure expressed by kPa or MPa, and the vertical axis represents an equilibrium adsorption amount expressed by mL(STP)/g. In the measurement results of adsorption/desorption isotherm, the adsorption amounts (ads.) of the gases (such as carbon dioxide, methane, nitrogen, ethane, or ethylene) under increased pressure and the adsorption amounts (des.) of the gases under decreased pressure are plotted for each pressure level. STP (Standard Temperature and Pressure) denotes a state at a temperature of 273.15 K and a pressure of 1 bar ($10^5$ Pa).

DESCRIPTION OF EMBODIMENTS

The metal complex of the present invention comprises a dicarboxylic acid compound (I) represented by the following General Formula (I); at least one metal ion selected from ions of a metal belonging to Group 2 and Groups 7 to 12 of the periodic table; and an organic ligand capable of bidentate binding to the metal ion, the organic ligand belonging to the $D_{\infty h}$ point group, having a longitudinal length of not less than 8.0 Å and less than 16.0 Å, and having 2 to 7 heteroatoms.

The metal complex can be produced by reacting a dicarboxylic acid compound (I), at least one metal selected from salts of a metal belonging to Group 2 and Groups 7 to 12 of the periodic table and an organic ligand capable of bidentate binding to the metal ion in a solvent under atmospheric pressure for several hours to several days to cause precipitation. The organic ligand capable of bidentate binding to the metal ion belongs to the $D_{\infty h}$ point group, has a longitudinal length of not less than 8.0 Å and less than 16.0 Å, and has 2 to 7 heteroatoms. For example, the metal complex of the present invention can be obtained by mixing and reacting an aqueous solution or an organic solvent solution of a metal salt with an organic solvent solution containing a dicarboxylic acid compound (I) and an organic ligand capable of bidentate binding under atmospheric pressure.

The dicarboxylic acid compound (I) of the present invention is represented by the following General Formula (I);

[Chem. 2]

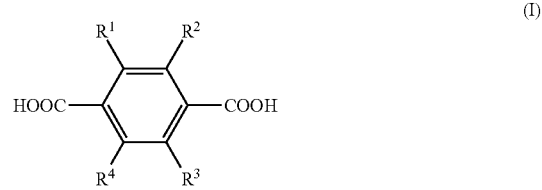

(I)

In the formula, $R^1$, $R^2$, $R^3$, and $R^4$ may be the same or different, and each independently represents a hydrogen atom, an alkyl group that may have a substituent, an alkoxy group, a formyl group, an acyloxy group, an alkoxycarbonyl group, a nitro group, a cyano group, an amino group, a monoalkylamino group, a dialkylamino group, an acylamino group or a halogen atom. Alternatively, either $R^1$ and $R^2$, or $R^3$ and $R^4$ may be taken together to form an alkylene or alkenylene group that may have a substituent.

Among the substituents constituting $R^1$, $R^2$, $R^3$, and $R^4$, the carbon number of the alkyl group or alkoxy group is preferably in a range of 1 to 5. Examples of alkyl group include linear or branched alkyl groups such as methyl, ethyl, n-propyl, isopropyl, n-butyl, isobutyl, tert-butyl, or pentyl. Examples of alkoxy group include methoxy, ethoxy, n-propoxy, isopropoxy, n-butoxy, isobutoxy, and tert-butoxy groups. Examples of acyloxy group include acetoxy, n-propanoyloxy, n-butanoyloxy, pivaloyloxy, and benzoyloxy groups. Examples of alkoxycarbonyl group include methoxy carbonyl, ethoxy carbonyl, and n-butoxycarbonyl groups. Examples of monoalkyl amino group include a methylamino group. Examples of dialkyl amino group include a dimethylamino group. Examples of acyl amino group include an acetyl amino group. Examples of halogen atom include fluorine atom, chlorine atom, bromine atom, and iodine atom. Further, examples of the substituents that the alkyl or other groups may have include alkoxy groups (such as methoxy, ethoxy, n-propoxy, isopropoxy, n-butoxy, isobutoxy, or tert-butoxy), amino group, monoalkyl amino group (such as methylamino), dialkyl amino group (such as dimethylamino), formyl group, epoxy group, acyloxy groups (such as acetoxy, n-propanoyloxy, n-butanoyloxy, pivaloyloxy, or benzoyloxy), alkoxycarbonyl groups (such as methoxycarbonyl, ethoxycarbonyl, or n-butoxycarbonyl), and carboxylic anhydride groups (—CO—O—CO—R groups in which R represents an alkyl group having 1 to 5 carbon atoms). The number of the substituents of the alkyl group is preferably from 1 to 3, more preferably 1.

The alkenylene preferably has two carbon atoms. In this case, $R^1$, $R^2$, $R^3$, and $R^4$ can be taken together with the carbon to which they are attached to form a four-membered ring (cyclobutene ring). Examples of such dicarboxylic acid compound (I) include a dihydrocyclobuta[1,2-b]terephthalic acid that may have a substituent.

The alkylene preferably has four carbon atoms. In this case, $R^1$, $R^2$, $R^3$, and $R^4$ can be taken together with the carbon to which they are attached to form a six-membered ring (benzene ring). Examples of such dicarboxylic acid compound (I) include a 1,4-naphthalene dicarboxylic acid that may have a substituent and a 9,10-anthracene dicarboxylic acid that may have a substituent.

Further, examples of the substituent that the alkylene and alkenylene groups may have include alkoxy groups (such as methoxy, ethoxy, n-propoxy, isopropoxy, n-butoxy, isobutoxy, or tert-butoxy), amino group, monoalkyl amino group (such as methylamino), dialkyl amino group (such as dimethylamino), formyl group, epoxy group, acyloxy groups (such as acetoxy, n-propanoyloxy, n-butanoyloxy, pivaloyloxy, or benzoyloxy), alkoxycarbonyl groups (such as methoxycarbonyl, ethoxycarbonyl, or n-butoxycarbonyl), and carboxylic anhydride groups (—CO—O—CO—R groups in which R represents an alkyl group having 1 to 5 carbon atoms).

Examples of usable dicarboxylic acid compound (I) include terephthalic acid (benzene-1,4-dicarboxylic acid), 2-methyl terephthalic acid, 2-methoxyterephthalic acid, 2-nitroterephthalic acid, dihydrocyclobuta[1,2-b]terephthalic acid, and 1,4-naphthalene dicarboxylic acid. Of these, terephthalic acid, 2-methylterephthalic acid, 2-mathoxyterephthalic acid, and 2-nitroterephthalic acid are preferable. 2-nitroterephthalic acid is more preferable.

The metal ion used in the present invention is at least one metal ion selected from ions of a metal belonging to of Group 2 and Groups 7 to 12 of the periodic table. The ions of a metal belonging to Group 2 of the periodic table includes a beryllium ion, a magnesium ion, a calcium ion, a strontium ion, a barium ion, and a radium ion. The ions of a metal belonging to Group 7 of the periodic table includes a manganese ion, a technetium ion, a rhenium ion, and a bohrium ion. The ions of a metal belonging to Group 8 of the periodic table includes an iron ion, a ruthenium ion, an osmium ion, and a hassium ion. The ions of a metal belonging to Group 9 of the periodic table includes a cobalt ion, a rhodium ion, an iridium ion and a meitnerium ion. The ions of a metal belonging to Group 10 of the periodic table includes a nickel ion, a palladium ion, a platinum ion and a darmstadtium ion. The ions of a metal belonging to Group 11 of the periodic table includes a copper ion, a silver ion, a gold ion and a roentgenium ion. The ions of a metal belonging to Group 12 of the periodic table includes a zinc ion, a cadmium ion, a mercury ion, and an ununbium ion. Among these ions of a metal belonging to Group 2 and Groups 7 to 12 of the periodic table, a magnesium ion, a calcium ion, a manganese ion, an iron ion, a ruthenium ion, a cobalt ion, a rhodium ion, a nickel ion, a palladium ion, a copper ion, a zinc ion, and a cadmium ion are preferable. A magnesium ion, a manganese ion, a cobalt ion, a nickel ion, a copper ion, a zinc ion, and a cadmium ion are more preferable. A zinc ion is particularly preferable. It is preferable to use one kind of metal ion; however, it is also possible to use two or more metal ions.

Examples of metal salts used for production of the metal complex include salts of a metal belonging to Group 2 and Groups 7 to 12 of the periodic table. Of these metal salts, a magnesium salt, a calcium salt, a manganese salt, an iron salt, a ruthenium salt, a cobalt salt, a rhodium salt, a nickel salt, a palladium salt, a copper salt, a zinc salt and a cadmium salt are preferable. A magnesium salt, a manganese salt, a cobalt salt, a nickel salt, a copper salt, a zinc salt, and a cadmium salt are more preferable. A zinc salt is particularly preferable. It is preferable to use one kind of metal salt; however, it is also possible to mix two or more metal salts. Further, the metal complex of the present invention may be produced by mixing two or more metal complexes, each of which is composed of one kind of metal ion. Examples of such metal salts include organic acid salts such as acetates or formates, and inorganic acid salts such as sulfates, nitrates, carbonates, hydrochlorides, or hydrobromates.

The organic ligand capable of bidentate binding used in the present invention belongs to the $D_{\infty h}$ point group, has a longitudinal length of not less than 8.0 Å and less than 16.0 Å, and has 2 to 7 heteroatoms. Here, the "organic ligand capable of bidentate binding" refers to a neutral ligand having two or more atoms coordinated to a metal ion with a lone electron pair.

The point group to which the organic ligand capable of bidentate binding belongs may be determined according to the method disclosed in Reference Document 1 below.

Reference Document 1: Bunshino Taisho to Gunron (Molecular Symmetry and Group Theory; Masao Nakazaki, 1973, Tokyo Kagaku Dojin Co., Ltd.) pp. 39-40.

For example, since 1,2-bis(4-pyridyl)ethyne, 1,4-bis(4-pyridyl)benzene, 3,6-di(4-pyridyl)-1,2,4,5-tetrazine, and 4,4'-bis(4-pyridyl)biphenyl are bilaterally symmetric linear molecules having a symmetric center, they belong to the $D_{\infty h}$ point group. Further, since 1,2-bis(4-pyridyl)ethene has a two-fold axis and symmetric planes perpendicular to the axis, it belongs to the $C_{2h}$ point group.

If the organic ligand capable of bidentate binding belongs to a point group other than $D_{\infty h}$, the symmetry decreases, thereby generating unwanted gaps, thus decreasing the adsorption amount.

The longitudinal length of the organic ligand capable of bidentate binding of the present specification is defined as the distance between two atoms having the longest distance therebetween among the atoms coordinated to the metal ion in the structural formula, in the most stable structure found by structure optimization according to the PM5 semiempirical molecular orbital method after the conformational analysis according to the MM3 molecular dynamics method using Scigress Explorer Professional Version 7.6.0.52 (produced by Fujitsu).

For example, the interatomic distance between nitrogen atoms of 1,4-diazabicyclo[2.2.2]octane is 2.609 Å, the interatomic distance between nitrogen atoms of pyrazine is 2.810 Å, the interatomic distance between nitrogen atoms of 4,4'-bipyridyl is 7.061 Å, the interatomic distance between nitrogen atoms of 1,2-bis(4-pyridyl)ethyne is 9.583 Å, the 1,4-bis(4-pyridyl)benzene interatomic distance between nitrogen atoms is 11.315 Å, the interatomic distance between nitrogen atoms of 3,6-di(4-pyridyl)-1,2,4,5-tetrazine is 11.204 Å, the interatomic distance between nitrogen atoms of 4,4'-bis(4-pyridyl)biphenyl is 15.570 Å, and the interatomic distance between nitrogen atoms of N,N'-di(4-pyridyl)-1,4,5,8-naphthalenetetracarboxydiimide is 15.533 Å.

When the longitudinal length of the organic ligand capable of bidentate binding is less than 8.0 Å, the micropore diameter becomes too small, thereby increasing the interaction with the pore wall, thus decreasing the selectivity. On the other hand, when the longitudinal length of the organic ligand capable of bidentate binding is 16.0 Å or greater, the micropore diameter becomes too large, thereby decreasing the interaction with the pore wall, thus decreasing the adsorption amount.

Examples of the heteroatoms contained in the organic ligand capable of bidentate binding of the present specification include nitrogen atom, oxygen atom, phosphorus atom, sulfur atom and the like.

For example, the number of heteroatoms contained in 1,2-bis(4-pyridyl)ethyne is 2, the number of heteroatoms contained in 1,4-bis(4-pyridyl)benzene is 2, the number of heteroatoms contained in 3,6-di(4-pyridyl)-1,2,4,5-tetrazine is 6, and the number of heteroatoms contained in N,N'-di(4-pyridyl)-1,4,5,8-naphthalenetetracarboxydiimide is 8.

When the organic ligand capable of bidentate binding has only one heteroatom, the ligand is incapable of bidentate binding to metal ions; therefore, the desired three-dimensional structure of a metal complex cannot be constructed. On the other hand, when the organic ligand capable of bidentate binding has eight or more heteroatoms, the charge density on the ligand that constitutes the pore wall increases the interaction between the gas molecules and the pore wall, thereby decreasing selectivity.

Examples of organic ligands capable of bidentate binding include 1,2-bis(4-pyridyl)ethyne, 1,4-bis(4-pyridyl)benzene, 3,6-di(4-pyridyl)-1,2,4,5-tetrazine, and 4,4'-bis(4-pyridyl)biphenyl. Of these, 1,2-bis(4-pyridyl)ethyne is preferable.

The proportion of dicarboxylic acid compound (I) relative to the organic ligand capable of bidentate binding in the metal complex is preferably in the following molar ratio: dicarboxylic acid compound (I):organic ligand capable of bidentate binding=2:3 to 3:1, more preferably 2:1.

The proportion of metal ion relative to the organic ligand capable of bidentate binding in the metal complex preferably falls in the following molar ratio: metal ion:organic ligand capable of bidentate binding=1:2 to 3:1, more preferably 2:1.

The mixing ratio of dicarboxylic acid compound (I) to the organic ligand capable of bidentate binding during the manufacture of the metal complex is preferably in the following molar ratio: dicarboxylic acid compound (I):organic ligand capable of bidentate binding=1:5 to 8:1, more preferably 1:3 to 6:1. If the mixing ratio falls out of this range during the reaction, the yield decreases and side reaction increases, even though the target metal complex can be obtained.

The mixing ratio of the metal salt to the organic ligand capable of bidentate binding during the manufacture of the metal complex preferably falls in the following molar ratio: metal salt:organic ligand capable of bidentate binding=3:1 to 1:3, more preferably 2:1 to 1:2. If the mixing ratio falls out of this range during the reaction, the yield of metal complex decreases and residues of unreacted material are generated, thereby causing complication in the purification process of the resulting metal complex.

The molar concentration of the dicarboxylic acid compound (I) in the solvent used for the manufacture of the metal complex is preferably 0.005 to 5.0 mol/L, more preferably 0.01 to 2.0 mol/L. If the molar concentration falls below this range upon the reaction, the yield of reaction undesirably decreases even though the target metal complex can still be obtained. If the molar concentration falls above this range upon the reaction, the solubility decreases, thereby hindering the progress of reaction.

The molar concentration of the metal salt in the solvent used for the manufacture of the metal complex is preferably 0.005 to 5.0 mol/L, more preferably 0.01 to 2.0 mol/L. If the molar concentration falls below this range upon the reaction, the yield of reaction undesirably decreases even though the target metal complex can still be obtained. If the molar concentration falls above this range, residues of unreacted metal salts are generated, thereby causing complication in the purification process of the resulting metal complex.

The molar concentration of the organic ligand capable of bidentate binding in the solvent used for the manufacture of the metal complex is preferably 0.001 to 5.0 mol/L, more preferably 0.005 to 2.0 mol/L. If the molar concentration falls below this range upon the reaction, the yield of reaction undesirably decreases even though the target metal complex can still be obtained. If the molar concentration falls above this range upon the reaction, the solubility decreases, thereby hindering the progress of reaction.

The solvent used for the manufacture of metal complex may be an organic solvent, water, or a mixed solvent of these. Specific examples of the solvents include methanol, ethanol, propanol, diethylether, dimethoxyethane, tetrahydrofuran, hexane, cyclohexane, heptane, benzene, toluene, methylene chloride, chloroform, acetone, acetic acidethyl, acetonitrile, N,N-dimethylformamide, water, and mixed solvents of these substances. The reaction temperature preferably falls in a range of 253 to 423 K.

A metal complex having a high crystallinity has high purity and ensures superior adsorption performance. The completion of the reaction may be confirmed by analyzing the remaining amount of the raw materials by using gas chromatography or high-performance liquid chromatography. After the reaction is completed, the resulting mixture is subjected to suction filtration to collect the precipitates. The precipitates are washed with an organic solvent and dried in vacuum for several hours at about 373 K, thereby yielding the metal complex of the present invention.

Figure 2:
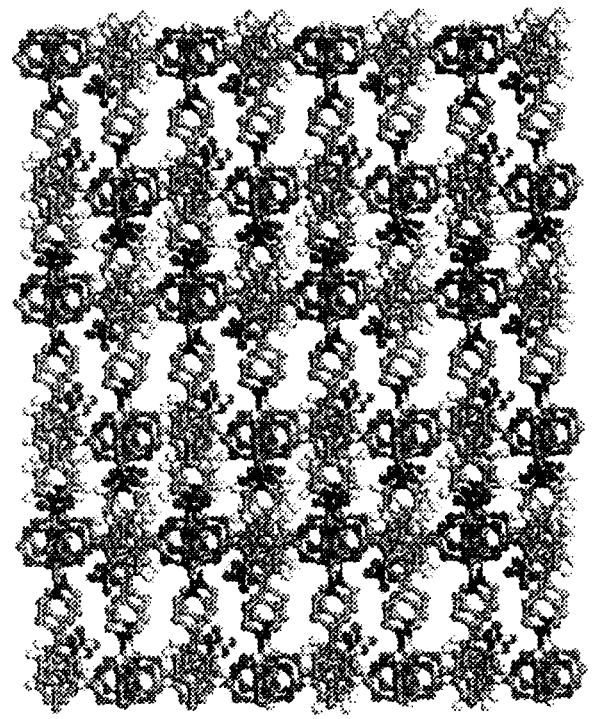
[FIG. 2] A schematic diagram illustrating a three-dimensional structure in which two jungle-gym-type frameworks are interpenetrated into each other.

The metal complex of the present invention thus obtained has a three-dimensional structure composed of interpenetrated multiple jungle-gym-type frameworks. The jungle-gym-type framework is structured such that an organic ligand capable of bidentate binding is coordinated to the axial position of a metal ion in a paddle-wheel-type framework composed of a metal ion and a carboxylate ion of the dicarboxylic acid compound (I). FIG. 1 is a schematic diagram illustrating a jungle-gym-type framework, and FIG. 2 is a schematic diagram illustrating a three-dimensional structure in which two jungle-gym-type frameworks are interpenetrated into each other.

In the present specification, "jungle-gym-type framework" is defined as a jungle-gym-like three-dimensional structure in which an organic ligand capable of bidentate binding is coordinated to the axial position of a metal ion in a paddle-wheel-type framework composed of a metal ion and a carboxylate ion of the dicarboxylic acid compound (I), thus connecting the two-dimensional lattice sheets composed of dicarboxylic acid compound (I) and the metal ion.

In the present specification, "a structure in which multiple jungle-gym-type frameworks are interpenetrated into each other" is defined as a three-dimensional framework in which two jungle-gym-type frameworks are interpenetrated into each other by filling each other's micropores.

For example, single-crystal X-ray crystal structure analysis or powder X-ray crystal structure analysis may be adopted to confirm whether the metal complex has the aforementioned structure in which multiple jungle-gym-type frameworks are interpenetrated into each other.

Figure 3:
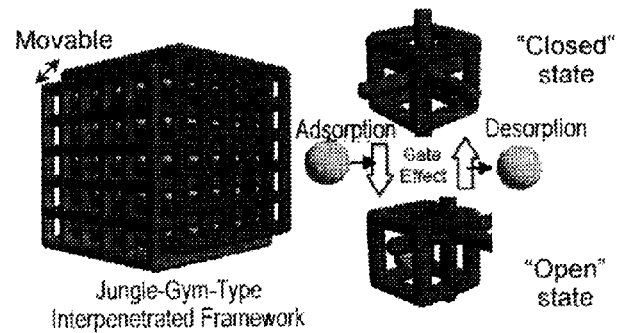
[FIG. 3] A schematic diagram illustrating structural change of the metal complex of the present invention upon adsorption and desorption.

The three-dimensional structure of the metal complex of the invention can also change in the crystal form after synthesis, and so with this change, the structure or the size of pores also changes. Conditions causing this structural change depend on the kind of a substance to be adsorbed, adsorption pressure, and adsorption temperature. This means that the degree of the structural change differs with a substance to be adsorbed as well as the difference in the interaction between the pore surface and the substance (the intensity of the interaction being in proportion to the magnitude of the Lennard-Jones potential of the substance), which leads to a high gas-adsorbing performance, a high gas-storing performance, and a high selectivity. FIG. 3 shows a schematic diagram illustrating structural change upon adsorption and desorption. The present invention ensures a high gas-adsorbing performance, a high gas-storing performance, and a high selectivity by controlling steric repulsion among the jungle-gym-type frameworks using the dicarboxylic acid compound represented by General Formula (I) and the organic ligand capable of bidentate binding represented by a General Formula. After desorption of the adsorbed substance, the structure of the metal complex returns to the original structure, and so the size of the pores also returns to the original size.

The above selective adsorption mechanism is estimated. Even if an adsorption mechanism does not conform to the above mechanism, it will be covered within the technical scope of the invention insofar as it satisfies the requirements specified in the invention.

Owing to its excellent adsorption performance with respect to various gases, the metal complex of the present invention is useful as an adsorbent material for adsorbing carbon dioxide, hydrogen, carbon monoxide, oxygen, nitrogen, hydrocarbons having from 1 to 4 carbon atoms (such as methane, ethane, ethylene, or acetylene), noble gases (such as helium, neon, argon, krypton, or xenon), hydrogen sulfide, ammonia, sulfur oxides, nitrogen oxides, siloxanes (such as hexamethylcyclotrisiloxane or octamethylcyclotetrasiloxane), water vapor, and organic vapor. The term "organic vapor" means a vaporizing gas of an organic substance that is in liquid form at ordinary temperature under ordinary pressure. Examples of such an organic substance include alcohols such as methanol and ethanol, amines such as trimethylamine, aldehydes such as acetaldehyde, aliphatic hydrocarbons having from 5 to 16 carbon atoms, aromatic hydrocarbons such as benzene and toluene, ketones such as acetone and methyl ethyl ketone, and halogenated hydrocarbons such as methyl chloride and chloroform.

Owing to its excellent adsorption performance with respect to various gases, the metal complex of the present invention is useful for an adsorption method for adsorbing carbon dioxide, hydrogen, carbon monoxide, oxygen, nitrogen, hydrocarbons having from 1 to 4 carbon atoms (such as methane, ethane, ethylene, or acetylene), noble gases (such as helium, neon, argon, krypton, or xenon), hydrogen sulfide, ammonia, sulfur oxides, nitrogen oxides, siloxanes (such as hexamethylcyclotrisiloxane or octamethylcyclotetrasiloxane), water vapor, and organic vapor.

The adsorption method comprises a step of bringing a gas and the metal complex of the present invention to be in contact with each other under the condition that enables the gas to be adsorbed to the metal complex. The condition, i.e., the adsorption pressure and the adsorption temperature that enable the gas to be adsorbed to the metal complex can be suitably set according to the type of the material to be adsorbed. For example, the adsorption pressure is preferably 1 to 100 kPa at 195 K (the temperature under which the saturated vapor pressure of the carbon dioxide becomes equal to the atmospheric pressure), and preferably 0.01 to 10 MPa at 273 K. The adsorption temperature is preferably 77 to 333 K, more preferably 195 to 313 K.

Owing to its excellent storing performance with respect to various gases, the metal complex of the present invention is useful as a storing material for storing carbon dioxide, hydrogen, carbon monoxide, oxygen, nitrogen, hydrocarbons having from 1 to 4 carbon atoms (such as methane, ethane, ethylene, or acetylene), noble gases (such as helium, neon, argon, krypton, or xenon), hydrogen sulfide, ammonia, water vapor, and organic vapor. The term "organic vapor" means a vaporizing gas of an organic substance that is in liquid form under ordinary pressure. Examples of such an organic substance include alcohols such as methanol and ethanol, amines such as trimethylamine, aldehydes such as acetaldehyde, aliphatic hydrocarbons having 5 to 16 carbon atoms, aromatic hydrocarbons such as benzene and toluene, ketones such as acetone and methyl ethyl ketone, and halogenated hydrocarbons such as methyl chloride and chloroform.

Owing to its excellent storing performance with respect to various gases, the metal complex of the present invention can also be used for a storing method for storing carbon dioxide, hydrogen, carbon monoxide, oxygen, nitrogen, hydrocarbons having from 1 to 4 carbon atoms (such as methane, ethane, ethylene, or acetylene), noble gases (such as helium, neon, argon, krypton, or xenon), hydrogen sulfide, ammonia, water vapor, and organic vapor.

The storing method comprises a step of bringing a gas and the metal complex of the present invention to be in contact with each other under the condition that enables the gas to be adsorbed to the metal complex. The condition, i.e., the adsorption pressure and the adsorption temperature that enable the gas to be adsorbed to the metal complex can be suitably set according to the type of the material to be adsorbed. For example, the adsorption pressure is preferably 1 to 100 kPa at 195 K, and preferably 0.01 to 10 MPa at 273 K. The adsorption temperature is preferably 77 to 333 K, more preferably 195 to 313 K.

The storing method further comprises a step of reducing the pressure from an adsorption pressure to a pressure enabling the gas to be desorbed from the metal complex. The condition, i.e., the desorption pressure, can be suitably set according to the type of the material to be adsorbed. For example, the desorption pressure is preferably 1 to 100 kPa at 195 K, and preferably 0.005 to 2 MPa at 273 K. The storing method otherwise comprises a step of increasing the temperature from an adsorption temperature to a temperature enabling the gas to be desorbed from the metal complex. The desorption temperature can be suitably set according to the type of the material to be adsorbed. For example, the desorption temperature is preferably 283 to 373 K.

Further, the metal complex of the present invention can selectively adsorb thereto various gases by controlling the adsorption pressure or the adsorption temperature, and so it is preferred as a separation material for separating carbon dioxide, hydrogen, carbon monoxide, oxygen, nitrogen, hydrocarbons having from 1 to 4 carbon atoms (such as methane, ethane, ethylene, or acetylene), noble gases (such as helium, neon, argon, krypton, or xenon), hydrogen sulfide, ammonia, sulfur oxides, nitrogen oxides, a siloxanes (such as hexamethylcyclotrisiloxane or octamethylcyclotetrasiloxane), water vapor, and organic vapor. In particular, it is suited for separating carbon dioxide from methane, carbon dioxide from hydrogen, carbon dioxide from nitrogen, ethane from methane, or methane from air by using a pressure swing adsorption process or a temperature swing adsorption process. The term "organic vapor" means a vaporizing gas of an organic substance that is in liquid form at ordinary temperature and ordinary pressure. Examples of such an organic substance include alcohols such as methanol and ethanol, amines such as trimethylamine, aldehydes such as acetaldehyde, aliphatic hydrocarbons having from 5 to 16 carbon atoms, aromatic hydrocarbons such as benzene and toluene, ketones such as methyl ethyl ketone, and halogenated hydrocarbons such as methyl chloride and chloroform.

Owing to its selective adsorption performance with respect to various gases, the metal complex of the present invention is useful for a separation method for separating carbon dioxide, hydrogen, carbon monoxide, oxygen, nitrogen, hydrocarbons having from 1 to 4 carbon atoms (such as methane, ethane, ethylene, or acetylene), noble gases (such as helium, neon, argon, krypton, or xenon), hydrogen sulfide, ammonia, sulfur oxides, nitrogen oxides, siloxanes (such as hexamethylcyclotrisiloxane or octamethylcyclotetrasiloxane), water vapor, and organic vapor.

The separation method comprises a step of bringing a gas and the metal complex of the present invention to be in contact with each other under the condition that enables the gas to be adsorbed to the metal complex. The condition, i.e., the adsorption pressure and the adsorption temperature that enable the gas to be adsorbed to the metal complex can be suitably set according to the type of the material to be adsorbed. For example, the adsorption pressure is preferably 1 to 100 kPa at 195 K, and preferably 0.01 to 10 MPa at 273 K. The adsorption temperature is preferably 77 to 333 K, more preferably 195 to 313 K.

The pressure swing adsorption process or the temperature swing adsorption process may be adopted as the separation method. When performing the pressure swing adsorption process as the separation method, the separation method further comprises a step of reducing the pressure from an adsorption pressure to a pressure enabling the gas to be desorbed from the metal complex. The desorption pressure may be suitably set according to the type of the material to be adsorbed. For example, the desorption pressure is preferably 1 to 100 kPa at 195 K, and preferably 0.005 to 2 MPa at 273 K. When performing the temperature swing adsorption process as the separation method, the separation method further comprises a step of increasing the temperature from an adsorption temperature to a temperature enabling the gas to be desorbed from the metal complex. The desorption temperature can be suitably set according to the type of the material to be adsorbed. For example, desorption temperature is preferably 283 to 373 K.

When performing the pressure swing adsorption process or the temperature swing adsorption process as the separation method, the step of bringing the gas to be in contact with the metal complex and the step of changing the pressure or the temperature that enable the gas to be desorbed from the metal complex may be appropriately repeated.

EXAMPLES

The invention will hereinafter be described specifically by using examples. It should be borne in mind, however, that the invention is not limited to or limited by these examples. The analysis and evaluation in the following Examples and Comparative Examples were conducted as described below.
(1) Single-Crystal X-Ray Crystal Structure Analysis The resulting single crystal was mounted on a gonio head and subjected to measurement using a single-crystal X-ray diffractometer.

The measurement conditions are shown below.
Analysis Conditions
Apparatus: SMART APEX II Ultra (trade name; product of Bruker AXS)
X-Ray Source: MoKα ($\lambda$=0.71073 Å) 50 kV 24 mA
Collection Mirror: HELIOS multilayer optics for Mo radiation
Detector: APEX II CCD
Collimator: Φ0.42 mm
Analysis Software: SHELX-97
(2) Powder X-Ray Diffraction Pattern Measurement The powder X-ray diffraction pattern was measured using an X-ray diffractometer based on the symmetric reflection method while scanning at a scanning rate of 1°/min within a diffraction angle (2θ) range of from 5 to 50°. Details of the measurement conditions are shown below.

Analysis Conditions
Apparatus: RINT-2400 (trade name; product of Rigaku Corporation)
X-ray Source: Cu Kα ($\lambda$=1.5418 Å) 40 kV 200 mA
Goniometer: Vertical Goniometer
Detector: Scintillation Counter
Step Width: 0.02°
Slit: Divergence Slit=0.5°
Receiving Slit=0.15 mm
Scattering Slit=0.5°
(3) Measurement of Adsorption/Desorption Isotherm (273 K)

An adsorption/desorption isotherm was measured based on the volumetric method by using a gas adsorption measuring instrument. Prior to the measurement, the sample was dried at 373 K and 50 Pa for 8 hours to remove adsorbed water and the like. The following are details of the measurement conditions.
Analysis Conditions
Apparatus: BELSORP-HP (trade name; product of Bel Japan, Inc.)
Equilibrium Waiting Time: 500 sec.
(4) Measurement of Adsorption/Desorption Isotherm (195 K)

An adsorption/desorption isotherm was measured based on the volumetric method by using a gas adsorption measuring instrument. Prior to the measurement, the sample was dried at 373 K and 50 Pa for 8 hours to remove adsorbed water and the like.

The following are details of the measurement conditions.
Analysis Conditions
Apparatus: BELSORP-18PLUS (trade name; product of Bel Japan, Inc.)
Equilibrium Waiting Time: 500 sec.

Synthesis Example 1

Figure 4:
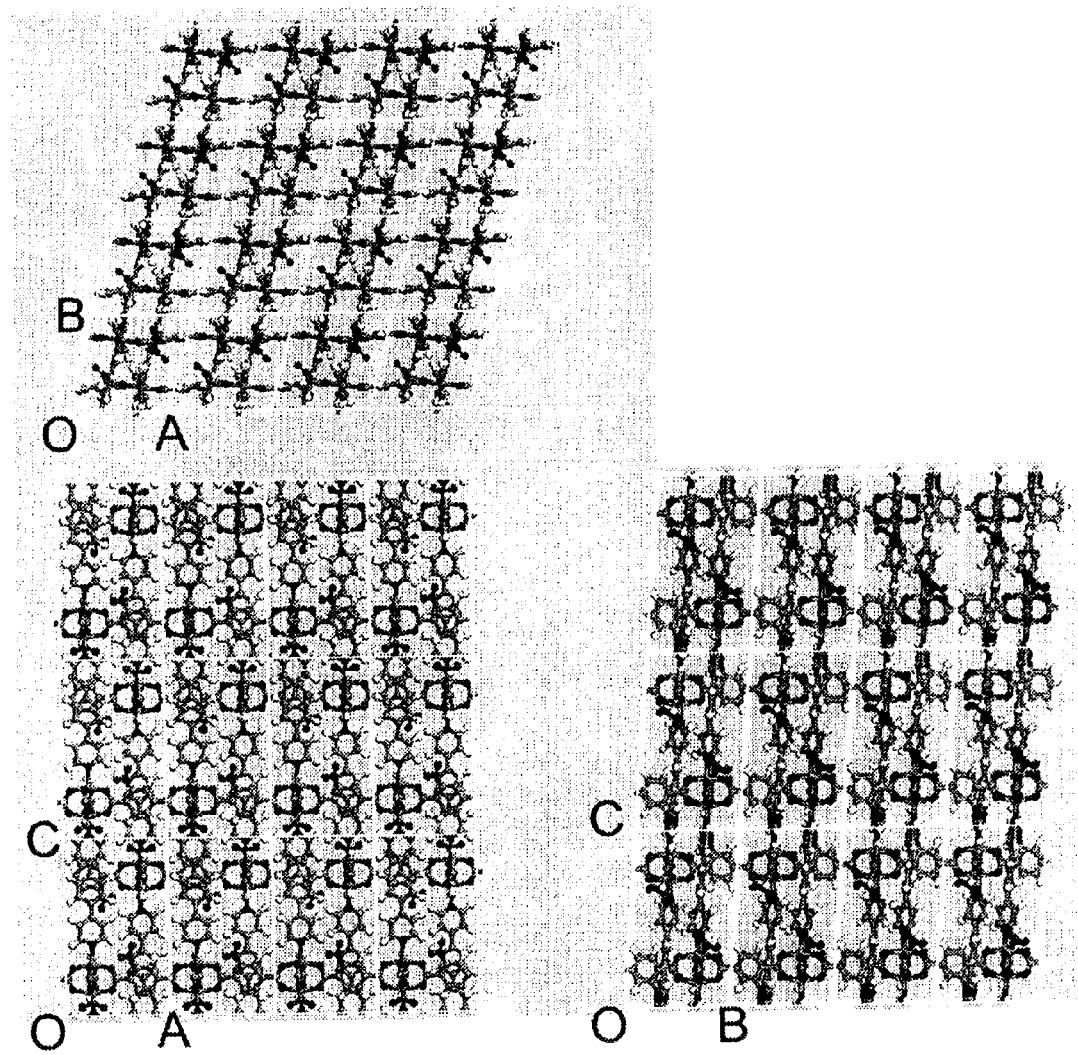
[FIG. 4] A crystal structure of a metal complex obtained in Synthesis Example 1. In the figure, the line O-A represents the a-axis, the line O-B represents the b-axis, and the line O-C represents the c-axis.
Figure 5:
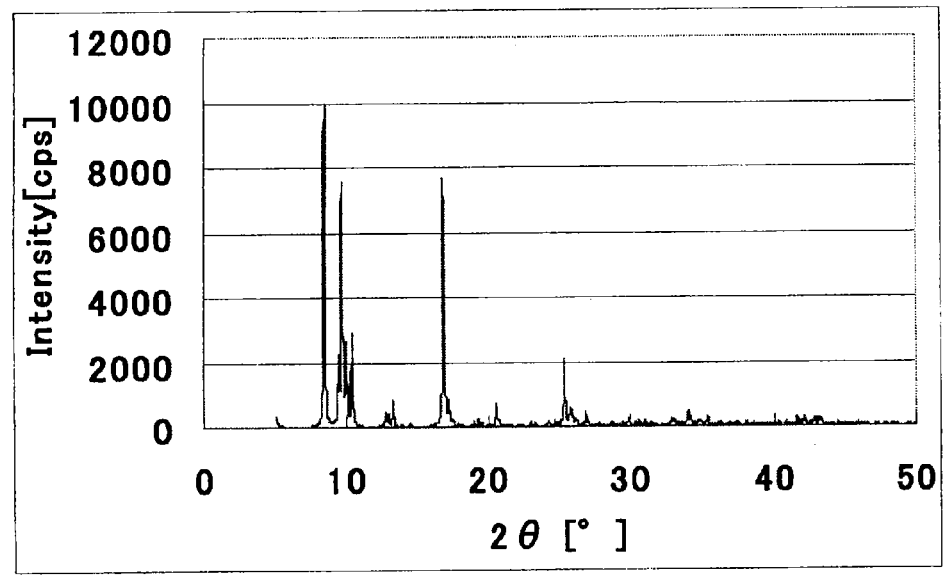
[FIG. 5] A powder X-ray diffraction pattern of a metal complex obtained in Synthesis Example 1 before vacuum drying.

Under nitrogen atmosphere, 4.37 g (15 mmol) of zinc nitrate hexahydrate, 3.10 g (15 mmol) of 2-nitroterephthalic acid, and 1.72 g (7.4 mmol) of 1,4-bis(4-pyridyl)benzene were dissolved in 600 mL of a mixed solvent containing N,N-dimethylformamide and benzene at a capacity ratio of 1:1. The mixture was stirred at 363 K for 24 hours. The resulting crystal was subjected to single-crystal X-ray crystal structure analysis. The result is shown below. The crystal structure is shown in FIG. 4. FIG. 4 revealed that the complex has a three-dimensional structure in which two jungle-gym-type frameworks, each of which contains dicarboxylic acid compound (I), a metal ion, and an organic ligand capable of bidentate binding at a ratio of 2:2:1, are interpenetrated into each other. FIG. 5 shows a powder X-ray diffraction pattern of the resulting metal complex.
Triclinic (P-1)
a=10.8583(18)Å (Axis OA in FIG. 4)
b=10.8772(18)Å (Axis OB in FIG. 4)
c=18.384(3)Å (Axis OC in FIG. 4)
α=86.110(3)°
β=89.874(3)°
γ=76.057(2)°
V=2102.2(6)Å$^3$
Z=2
R=0.1612
Rw=0.4239

Figure 6:
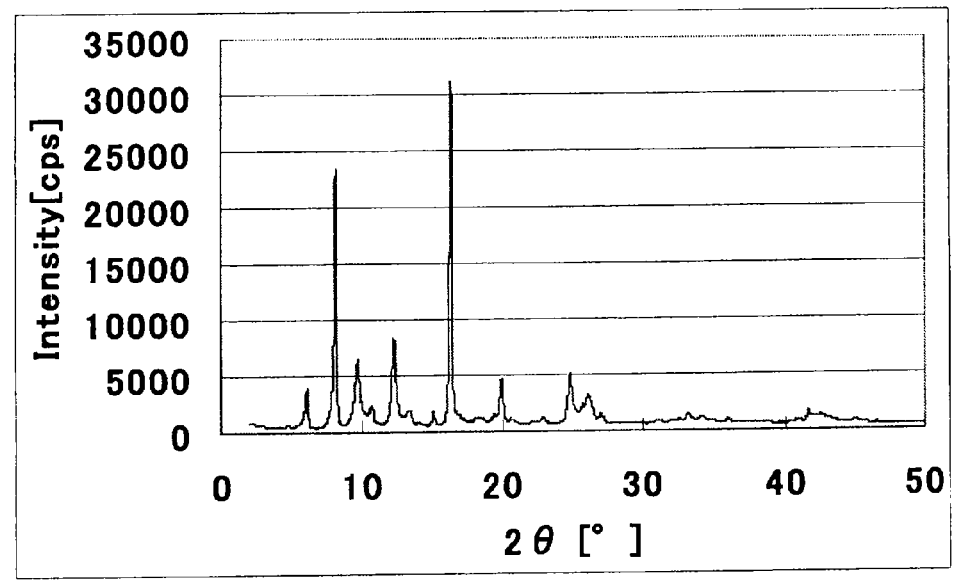
[FIG. 6] A powder X-ray diffraction pattern of a metal complex obtained in Synthesis Example 1 after vacuum drying.

After collecting the precipitated metal complex by suction filtration, the metal complex was washed three times with methanol. Subsequently, the metal complex was dried for 8 hours at 373 K, 50 Pa, thereby obtaining 4.21 g of the target metal complex (yield=73%). The powder X-ray diffraction pattern of the metal complex thus obtained is shown in FIG. 6. The comparison between FIG. 5 and FIG. 6 revealed that the powder X-ray diffraction pattern changes before and after the adsorption/desorption of the synthetic solvent. This shows that the structure of the metal complex of the present invention dynamically changes due to the adsorption/desorption.

Synthesis Example 2

Figure 7:
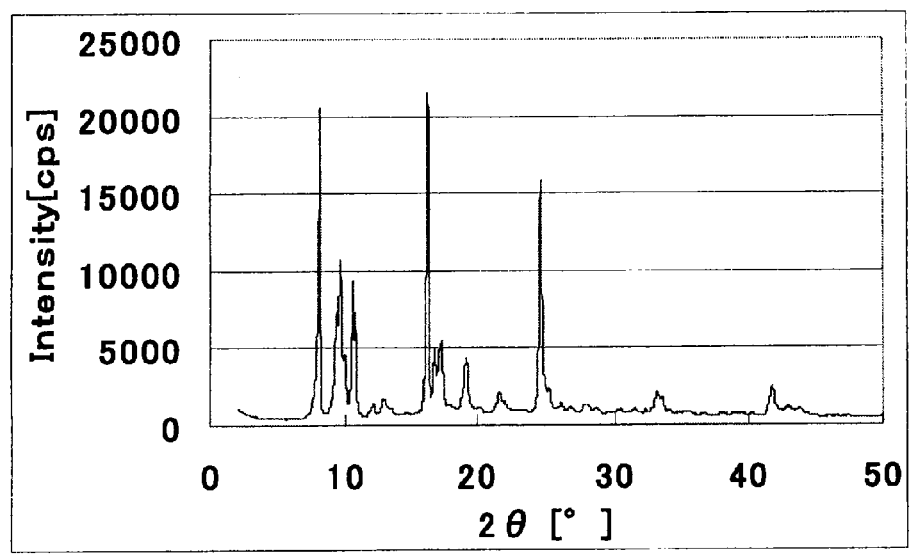
[FIG. 7] A powder X-ray diffraction pattern of a metal complex obtained in Synthesis Example 2 before vacuum drying.
Figure 8:
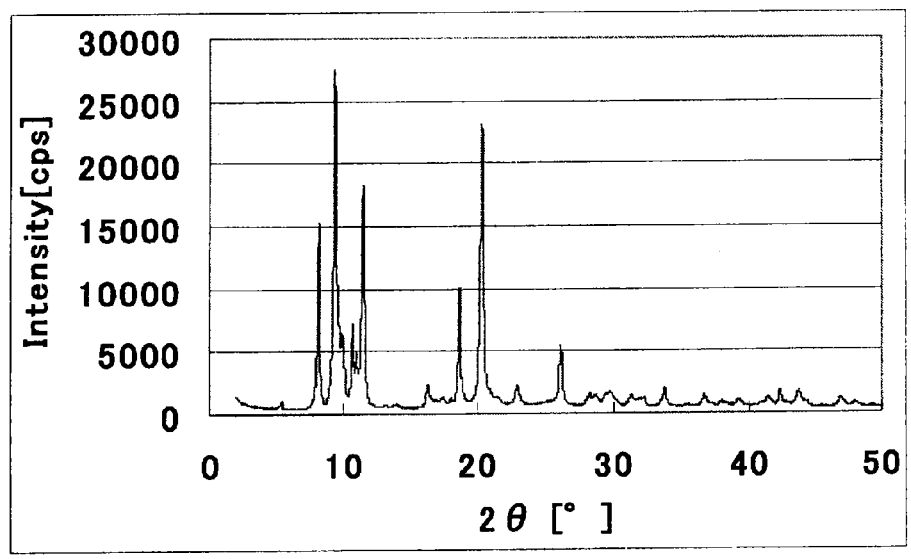
[FIG. 8] A powder X-ray diffraction pattern of a metal complex obtained in Synthesis Example 2 after vacuum drying.

Under nitrogen atmosphere, 10.1 g (34 mmol) of zinc nitrate hexahydrate, 7.14 g (34 mmol) of 2-nitroterephthalic acid, and 3.04 g (17 mmol) of 1,2-bis(4-pyridyl)ethyne were dissolved in 1380 mL of N,N-dimethylformamide. The mixture was stirred at 363 K for 24 hours. The resulting crystal was subjected to single-crystal X-ray crystal structure analysis. The result revealed that the complex has a three-dimensional structure in which two jungle-gym-type frameworks, each of which contains a dicarboxylic acid compound (I), a metal ion, and an organic ligand capable of bidentate binding at a ratio of 2:2:1, are interpenetrated into each other. FIG. 7 shows a powder X-ray diffraction pattern of the resulting metal complex. After collecting the precipitated metal complex by suction filtration, the metal complex was washed three times with methanol. Subsequently, the metal complex was dried for 8 hours at 373 K, Pa, thereby obtaining 8.87 g of the target metal complex (yield=72%). The powder X-ray diffraction pattern of the metal complex thus obtained is shown in FIG. 8. The comparison between FIG. 7 and FIG. 8 revealed that the powder X-ray diffraction pattern changes before and after the adsorption/desorption of the synthetic solvent. This shows that the structure of the metal complex of the present invention dynamically changes due to the adsorption/desorption.

Synthesis Example 3

Figure 9:
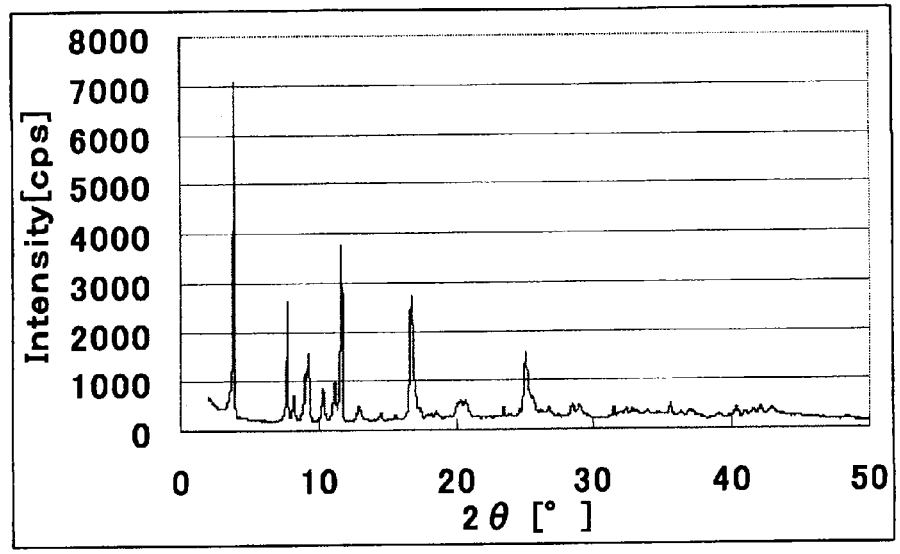
[FIG. 9] A powder X-ray diffraction pattern of a metal complex obtained in Synthesis Example 3 before vacuum drying.
Figure 10:
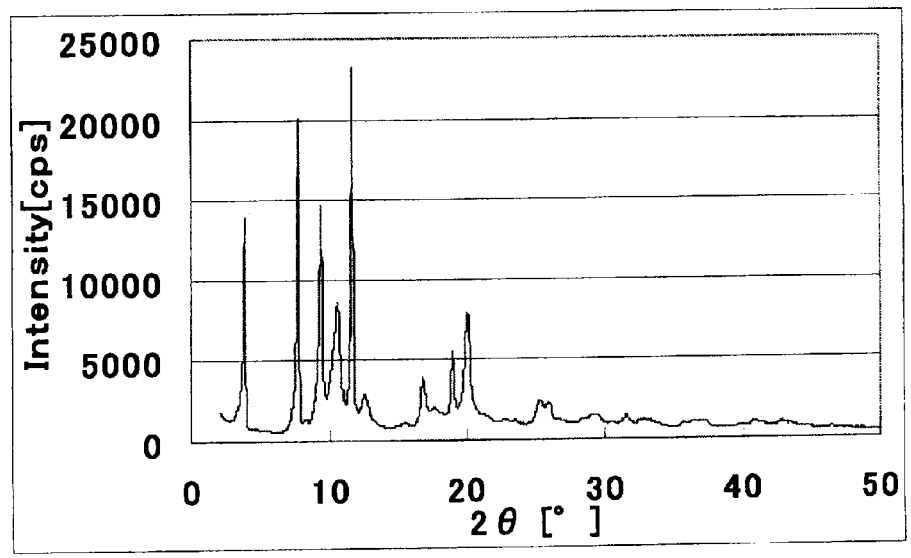
[FIG. 10] A powder X-ray diffraction pattern of a metal complex obtained in Synthesis Example 3 after vacuum drying.

Under nitrogen atmosphere, 2.81 g (9.5 mmol) of zinc nitrate hexahydrate, 2.00 g (9.5 mmol) of 2-nitroterephthalic acid, and 1.44 g (4.7 mmol) of 4,4-bis(4-pyridyl)biphenyl were dissolved in 380 mL of a mixed solvent containing N,N-dimethylformamide and benzene at a capacity ratio of 1:1. The mixture was stirred at 363 K for 24 hours. The resulting crystal was subjected to single-crystal X-ray crystal structure analysis. The result revealed that the complex has a three-dimensional structure in which two jungle-gym-type frameworks, each of which contains a dicarboxylic acid compound (I), a metal ion, and an organic ligand capable of bidentate binding at a ratio of 2:2:1, are interpenetrated into each other. FIG. 9 shows a powder X-ray diffraction pattern of the resulting metal complex. After collecting the precipitated metal complex by suction filtration, the metal complex was washed three times with methanol. Subsequently, the metal complex was dried for 8 hours at 373 K, 50 Pa, thereby obtaining 2.62 g of the target metal complex (yield=65%). The powder X-ray diffraction pattern of the metal complex thus obtained is shown in FIG. 10. The comparison between FIG. 9 and FIG. 10 revealed that the powder X-ray diffraction pattern changes before and after the adsorption/desorption of the synthetic solvent. This shows that the structure of the metal complex of the present invention dynamically changes due to the adsorption/desorption.

Synthesis Example 4

Figure 11:
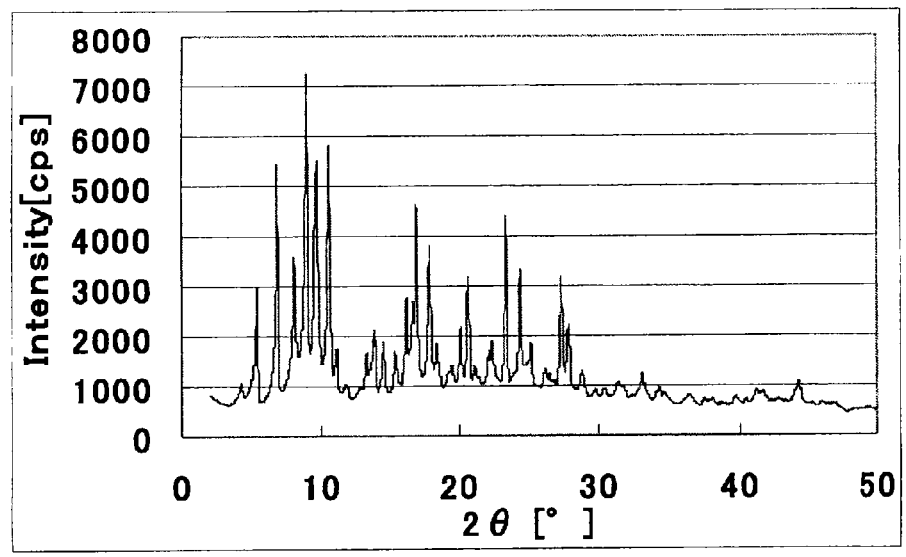
[FIG. 11] A powder X-ray diffraction pattern of a metal complex obtained in Synthesis Example 4 before vacuum drying.
Figure 12:
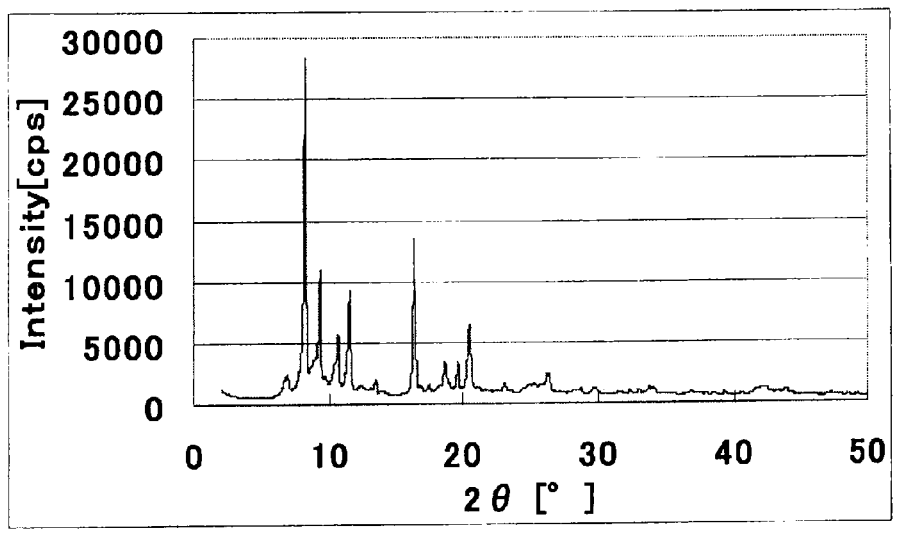
[FIG. 12] A powder X-ray diffraction pattern of a metal complex obtained in Synthesis Example 4 after vacuum drying.

Under nitrogen atmosphere, 2.82 g (9.5 mmol) of zinc nitrate hexahydrate, 1.86 g (9.5 mmol) of 2-methoxyterephthalic acid, and 0.85 g (4.7 mmol) of 1,2-bis(4-pyridyl)ethyne were dissolved in 800 ml of a mixed solvent containing N,N-dimethylformamide and ethanol at a capacity ratio of 1:1. The mixture was stirred at 363 K for 48 hours. The resulting crystal was subjected to single-crystal X-ray crystal structure analysis. The result revealed that the complex has a three-dimensional structure in which two jungle-gym-type frameworks, each of which contains a dicarboxylic acid compound (I), a metal ion, and an organic ligand capable of bidentate binding at a ratio of 2:2:1, are interpenetrated into each other. FIG. 11 shows a powder X-ray diffraction pattern of the resulting metal complex. After collecting the precipitated metal complex by suction filtration, the metal complex was washed three times with methanol. Subsequently, the metal complex was dried for 8 hours at 373 K, 50 Pa, thereby obtaining 2.73 g of the target metal complex (yield=82%). The powder X-ray diffraction pattern of the metal complex thus obtained is shown in FIG. 12. The comparison between FIG. 11 and FIG. 12 revealed that the powder X-ray diffraction pattern changes before and after the adsorption/desorption of the synthetic solvent. This shows that the structure of the metal complex of the present invention dynamically changes due to the adsorption/desorption.

Synthesis Example 5

Figure 13:
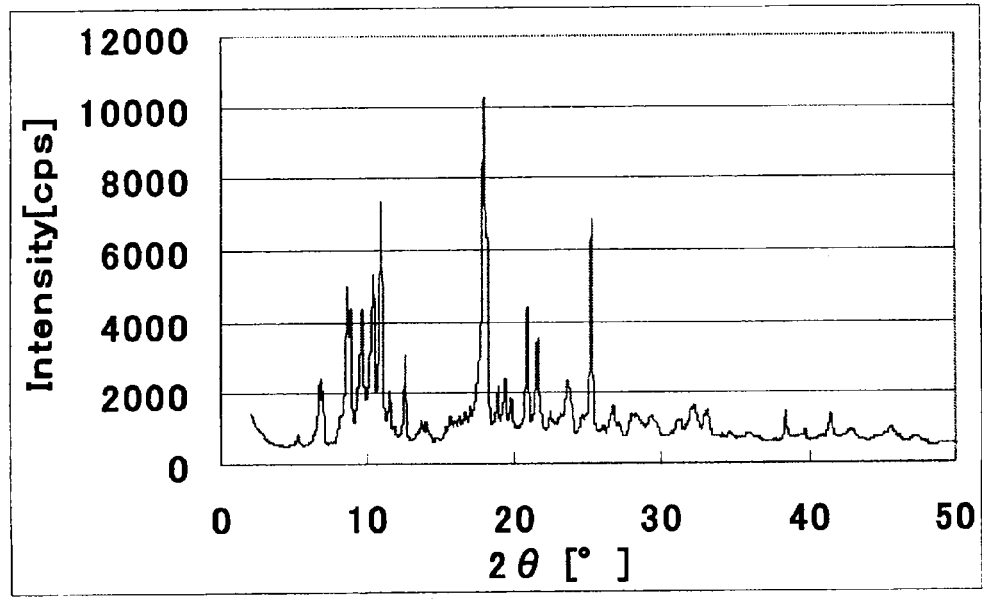
[FIG. 13] A powder X-ray diffraction pattern of a metal complex obtained in Synthesis Example 5 before vacuum drying.
Figure 14:
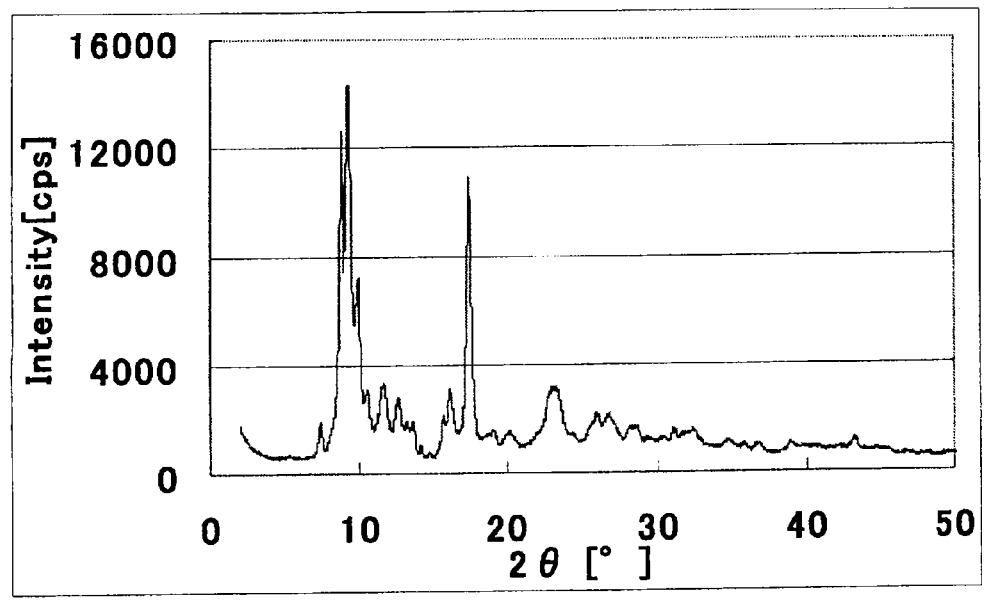
[FIG. 14] A powder X-ray diffraction pattern of a metal complex obtained in Synthesis Example 5 after vacuum drying.

Under nitrogen atmosphere, 2.81 g (9.5 mmol) of zinc nitrate hexahydrate, 1.57 g (9.5 mmol) of terephthalic acid, and 0.852 g (4.7 mmol) of 1,2-bis(4-pyridyl)ethyne were dissolved in 800 mL of a mixed solvent containing N,N-dimethylformamide and ethanol at a capacity ratio of 1:1. The mixture was stirred at 363 K for 48 hours. The resulting crystal was subjected to single-crystal X-ray crystal structure analysis. The result revealed that the complex has a three-dimensional structure in which two jungle-gym-type frameworks, each of which contains a dicarboxylic acid compound (I), a metal ion, and an organic ligand capable of bidentate binding at a ratio of 2:2:1, are interpenetrated into each other. FIG. 13 shows a powder X-ray diffraction pattern of the resulting metal complex. After collecting the precipitated metal complex by suction filtration, the metal complex was washed three times with methanol. Subsequently, the metal complex was dried for 8 hours at 373 K, 50 Pa, thereby obtaining 2.65 g of the target metal complex (yield=88%). The powder X-ray diffraction pattern of the metal complex thus obtained is shown in FIG. 14. The comparison between FIG. 13 and FIG. 14 revealed that the powder X-ray diffraction pattern changes before and after the adsorption/desorption of the synthetic solvent. This shows that the structure of the metal complex of the present invention dynamically changes due to the adsorption/desorption.

Synthesis Example 6

Figure 15:
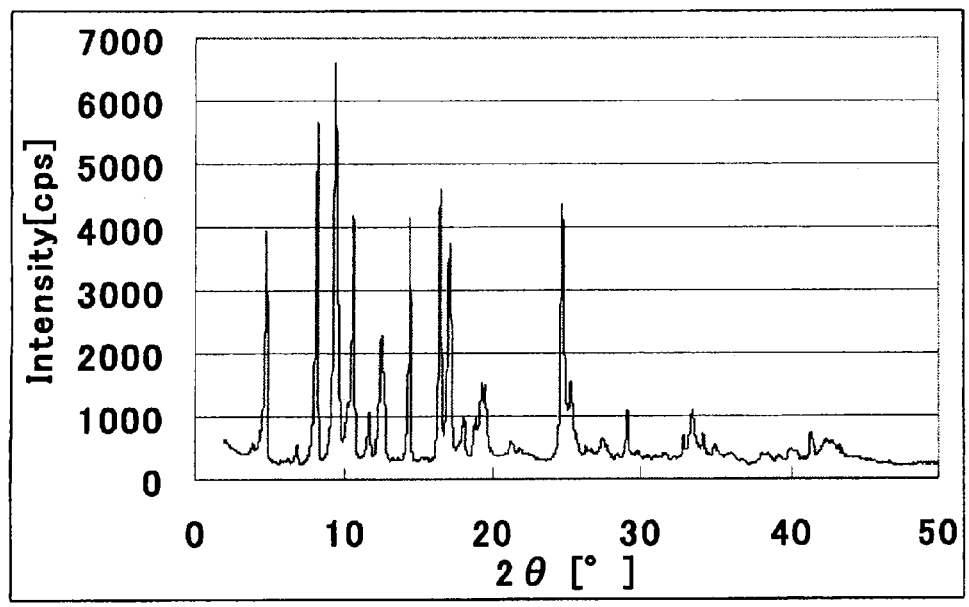
[FIG. 15] A powder X-ray diffraction pattern of a metal complex obtained in Synthesis Example 6 before vacuum drying.
Figure 16:
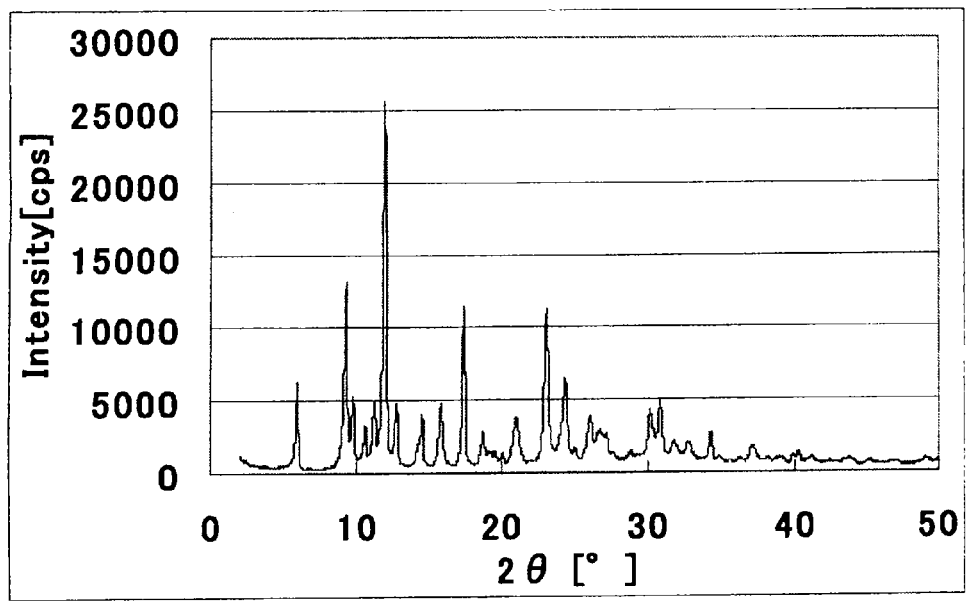
[FIG. 16] A powder X-ray diffraction pattern of a metal complex obtained in Synthesis Example 6 after vacuum drying.

Under nitrogen atmosphere, 2.81 g (9.5 mmol) of zinc nitrate hexahydrate, 1.57 g (9.5 mmol) of terephthalic acid, and 1.10 g (4.7 mmol) of 1,4-bis(4-pyridyl)benzene were dissolved in 800 mL of a mixed solvent containing N,N-dimethylformamide and ethanol at a capacity ratio of 1:1. The mixture was stirred at 363 K for 24 hours. The resulting crystal was subjected to single-crystal X-ray crystal structure analysis. The result revealed that the complex has a three-dimensional structure in which two jungle-gym-type frameworks, each of which contains a dicarboxylic acid compound (I), a metal ion, and an organic ligand capable of bidentate binding at a ratio of 2:2:1, are interpenetrated into each other. FIG. 15 shows a powder X-ray diffraction pattern of the resulting metal complex. After collecting the precipitated metal complex by suction filtration, the metal complex was washed three times with methanol. Subsequently, the metal complex was dried for 8 hours at 373 K, 50 Pa, thereby obtaining 3.01 g of the target metal complex (yield=92%). The powder X-ray diffraction pattern of the metal complex thus obtained is shown in FIG. 16. The comparison between FIG. 15 and FIG. 16 revealed that the powder X-ray diffraction pattern changes before and after the adsorption/desorption of the synthetic solvent. This shows that the structure of the metal complex of the present invention dynamically changes due to the adsorption/desorption.

Comparative Synthesis Example 1

Figure 17:
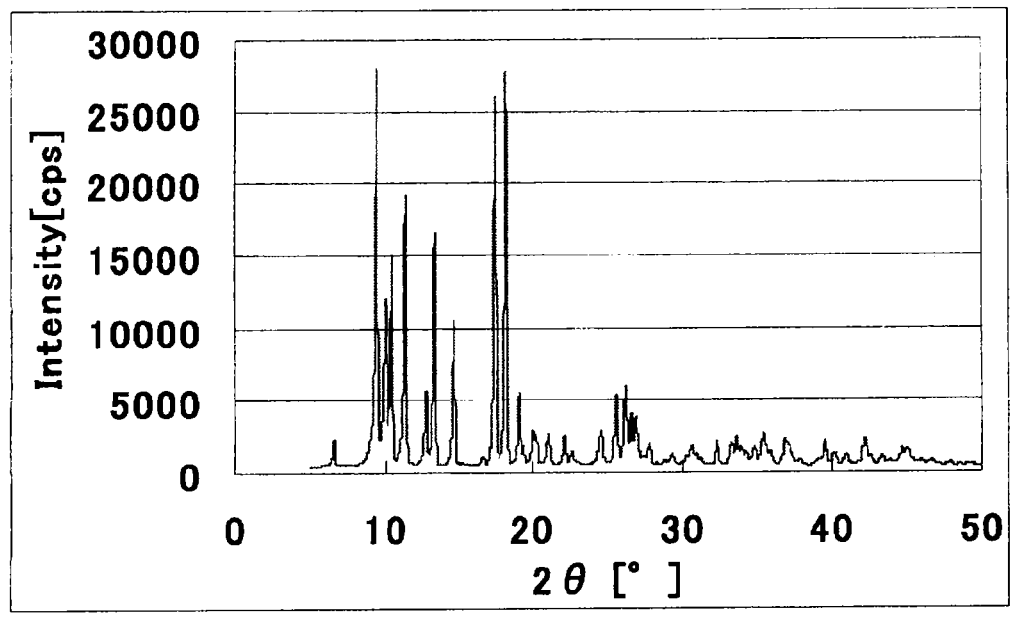
[FIG. 17] A powder X-ray diffraction pattern of a metal complex obtained in Comparative Synthesis Example 1 after vacuum drying.

Under nitrogen atmosphere, 2.81 g (9.5 mmol) of zinc nitrate hexahydrate, 2.00 g (9.5 mmol) of 2-nitroterephthalic acid, and 0.739 g (4.7 mmol) of 4,4'-bipyridyl were dissolved in 800 mL of a mixed solvent containing N,N-dimethylformamide and ethanol at a capacity ratio of 1:1. The mixture was stirred at 363 K for 48 hours. After collecting the precipitated metal complex by suction filtration, the metal complex was washed three times with methanol. Subsequently, the metal complex was dried for 8 hours at 373 K, 50 Pa, thereby obtaining 2.89 g of the target metal complex (yield=87%). The powder X-ray diffraction pattern of the metal complex thus obtained is shown in FIG. 17.

Comparative Synthesis Example 2

Figure 18:
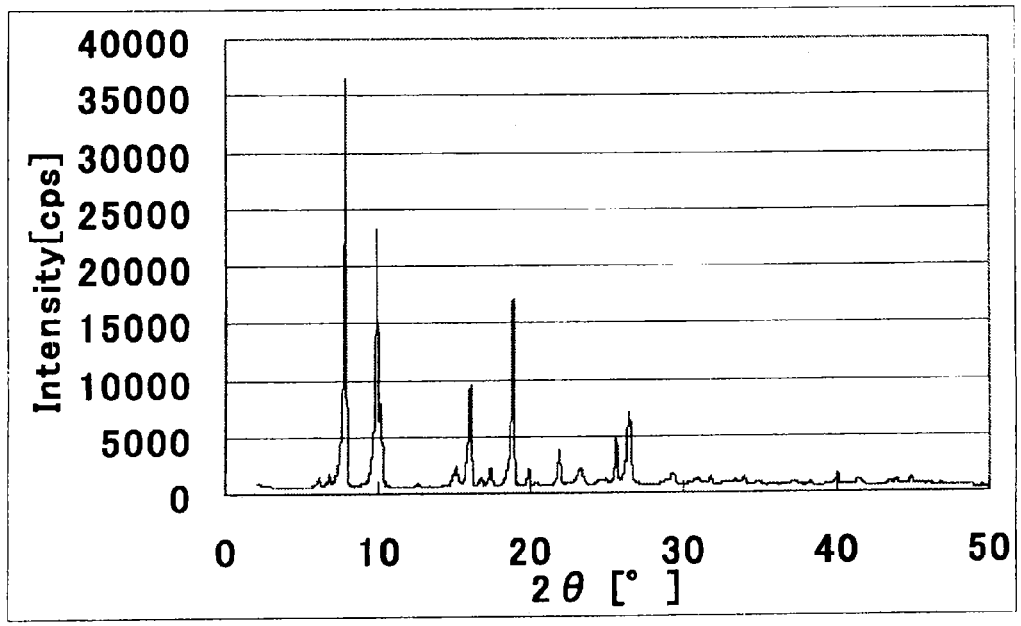
[FIG. 18] A powder X-ray diffraction pattern of a metal complex obtained in Comparative Synthesis Example 2 after vacuum drying.

Under nitrogen atmosphere, 1.78 g (6.0 mmol) of zinc nitrate hexahydrate, 1.27 g (6.0 mmol) of 2-nitroterephthalic acid, and 1.26 g (3.0 mmol) of N,N'-di(4-pyridyl)-1,4,5,8-naphthalenetetracarboxydiimide were dissolved in 540 ml of a mixed solvent containing N,N-dimethylformamide and ethanol at a capacity ratio of 1:1. The mixture was stirred at 363 K for 24 hours. After collecting the precipitated metal complex by suction filtration, the metal complex was washed three times with methanol. Subsequently, the metal complex was dried for 8 hours at 373 K, 50 Pa, thereby obtaining 2.66 g of the target metal complex (yield=91%). The powder X-ray diffraction pattern of the metal complex thus obtained is shown in FIG. 18.

Comparative Synthesis Example 3

Figure 19:
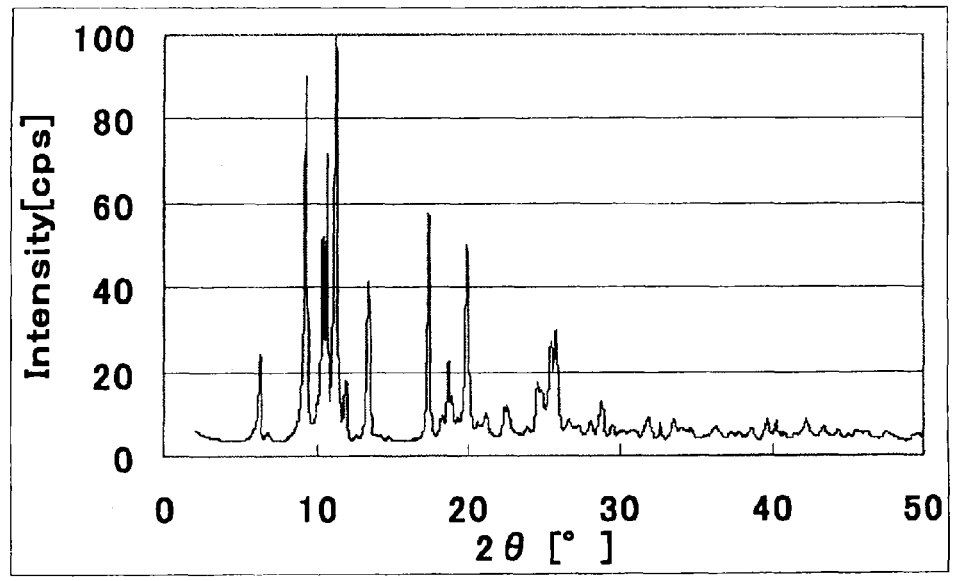
[FIG. 19] A powder X-ray diffraction pattern of a metal complex obtained in Comparative Synthesis Example 3 after vacuum drying.

Under nitrogen atmosphere, 2.82 g (9.5 mmol) of zinc nitrate hexahydrate, 1.86 g (9.5 mmol) of 2-methoxyterephthalic acid, and 0.87 g (4.7 mmol) of trans-1,2-bis(4-pyridyl)ethene were dissolved in 800 mL of a mixed solvent containing N,N-dimethylformamide and ethanol at a capacity ratio of 1:1. The mixture was stirred at 363 K for 24 hours. After collecting the precipitated metal complex by suction filtration, the metal complex was washed three times with methanol. Subsequently, the metal complex was dried for 8 hours at 373 K, 50 Pa, thereby obtaining 2.87 g of the target metal complex (yield=86%). The powder X-ray diffraction pattern of the metal complex thus obtained is shown in FIG. 19.

Comparative Synthesis Example 4

Figure 20:
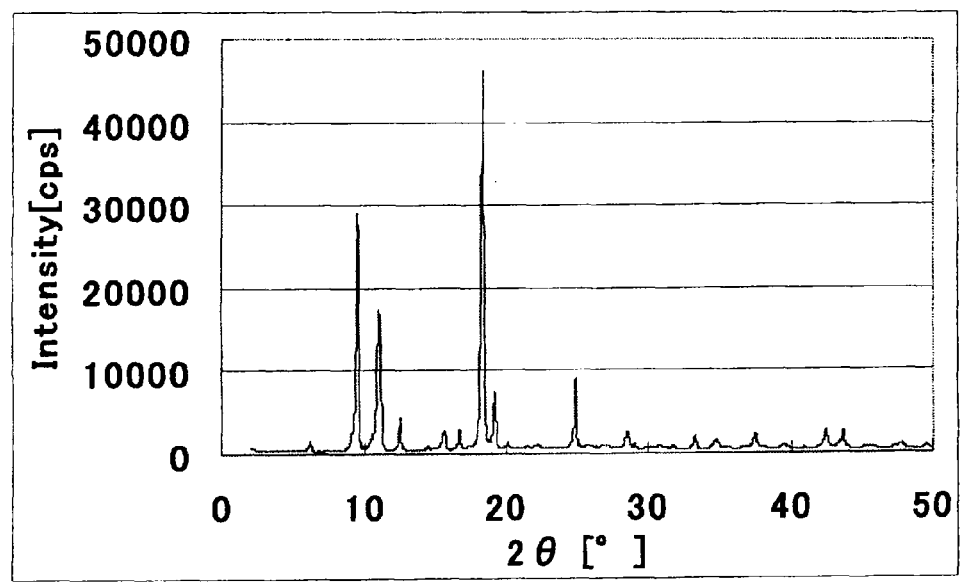
[FIG. 20] A powder X-ray diffraction pattern of a metal complex obtained in Comparative Synthesis Example 4 after vacuum drying.

Under nitrogen atmosphere, 2.81 g (9.5 mmol) of zinc nitrate hexahydrate, 1.85 g (9.5 mmol) of 2-methoxyterephthalic acid, and 0.74 g (4.7 mmol) of 4,4'-bipyridyl were dissolved in 800 mL of a mixed solvent containing N,N-dimethylformamide and ethanol at a capacity ratio of 1:1. The mixture was stirred at 363 K for 24 hours. After collecting the precipitated metal complex by suction filtration, the metal complex was washed three times with methanol. Subsequently, the metal complex was dried for 8 hours at 373 K, 50 Pa, thereby obtaining 2.28 g of the target metal complex (yield=71%). The powder X-ray diffraction pattern of the metal complex thus obtained is shown in FIG. 20.

Comparative Synthesis Example 5

Figure 21:
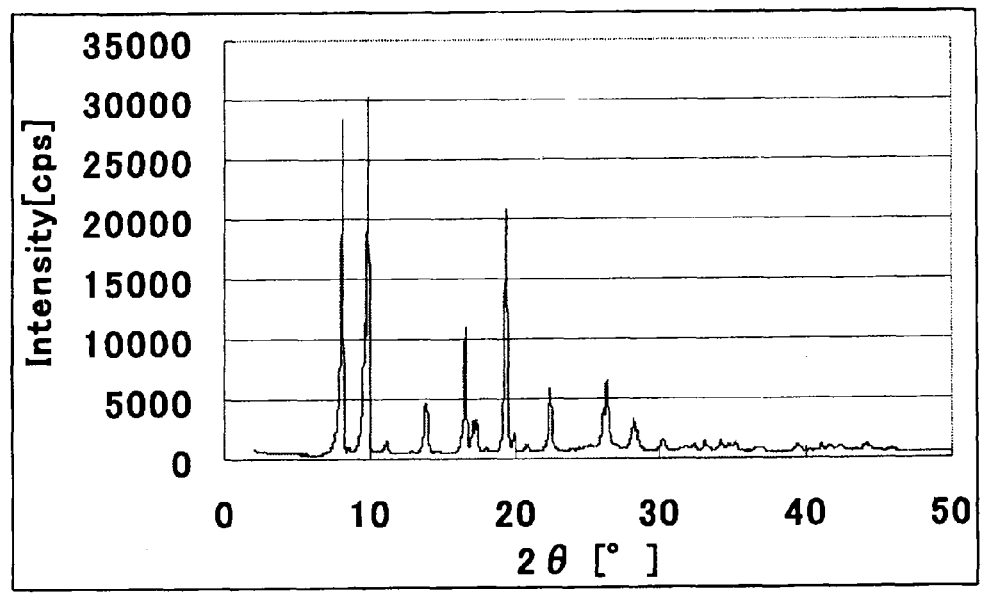
[FIG. 21] A powder X-ray diffraction pattern of a metal complex obtained in Comparative Synthesis Example 5 after vacuum drying.

Under nitrogen atmosphere, 1.78 g (6.0 mmol) of zinc nitrate hexahydrate, 1.18 g (3.0 mmol) of 2-methoxyterephthalic acid, and 1.26 g (3.0 mmol) of N,N'-di(4-pyridyl)-1,4,5,8-naphthalenetetracarboxydiimide were dissolved in 540 mL of a mixed solvent containing N,N-dimethylformamide and ethanol at a capacity ratio of 1:1. The mixture was stirred at 363 K for 24 hours. After collecting the precipitated metal complex by suction filtration, the metal complex was washed three times with methanol. Subsequently, the metal complex was dried for 8 hours at 373 K, 50 Pa, thereby obtaining 2.23 g of the target metal complex (yield=79%). The powder X-ray diffraction pattern of the metal complex thus obtained is shown in FIG. 21.

Comparative Synthesis Example 6

Figure 22:
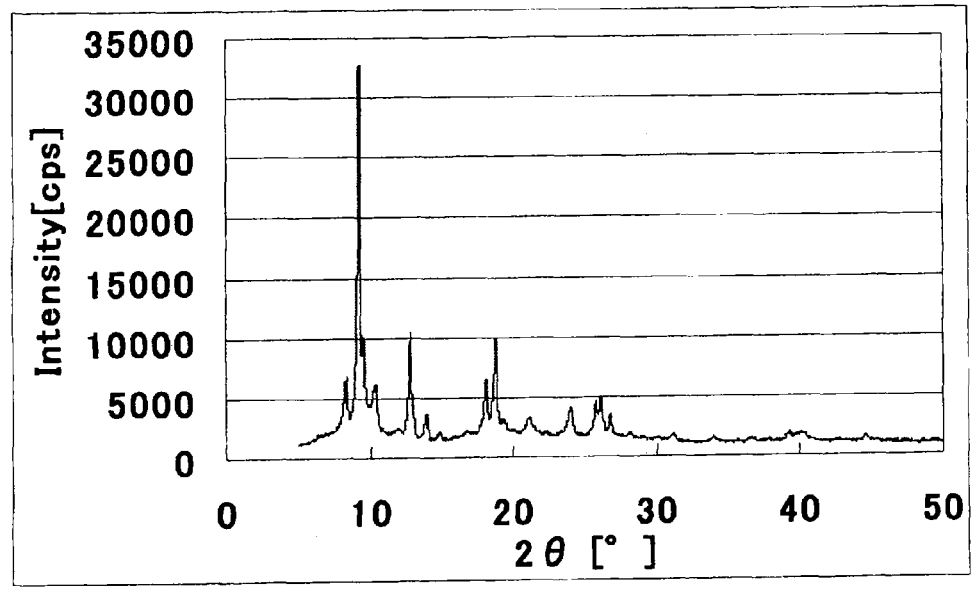
[FIG. 22] A powder X-ray diffraction pattern of a metal complex obtained in Comparative Synthesis Example 6 after vacuum drying.

Under nitrogen atmosphere, 5.00 g (17 mmol) of zinc nitrate hexahydrate, 2.80 g (17 mmol) of isophthalic acid, and 3.03 g (17 mmol) of 1,2-bis(4-pyridyl)ethyne were dissolved in 200 mL of N,N-dimethylformamide. The mixture was stirred at 363 K for 24 hours. After collecting the precipitated metal complex by suction filtration, the metal complex was washed three times with methanol. Subsequently, the metal complex was dried for 8 hours at 373 K, 50 Pa, thereby obtaining 3.50 g of the target metal complex (yield=51%). The powder X-ray diffraction pattern of the metal complex thus obtained is shown in FIG. 22.

Comparative Synthesis Example 7

Figure 23:
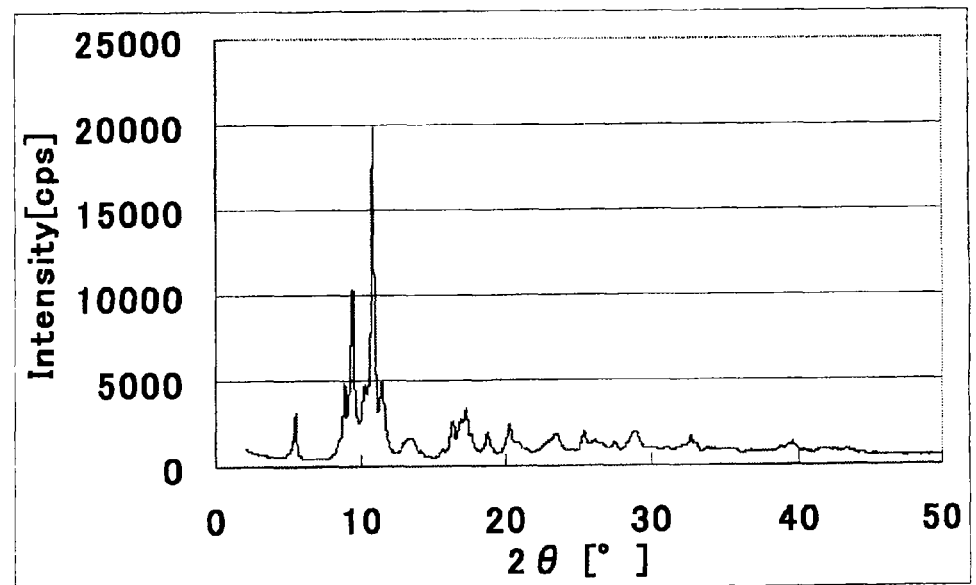
[FIG. 23] A powder X-ray diffraction pattern of a metal complex obtained in Comparative Synthesis Example 7 after vacuum drying.

Under nitrogen atmosphere, 2.81 g (9.5 mmol) of zinc nitrate hexahydrate, 1.57 g (9.5 mmol) of terephthalic acid, and 0.862 g (4.7 mmol) of trans-1,2-bis(4-pyridyl)ethene were dissolved in 800 mL of a mixed solvent containing N,N-dimethylformamide and ethanol at a capacity ratio of 1:1. The mixture was stirred at 363 K for 48 hours. After collecting the precipitated metal complex by suction filtration, the metal complex was washed three times with methanol. Subsequently, the metal complex was dried for 8 hours at 373 K, 50 Pa, thereby obtaining 2.89 g of the target metal complex (yield=95%). The powder X-ray diffraction pattern of the metal complex thus obtained is shown in FIG. 23.

Comparative Synthesis Example 8

Figure 24:
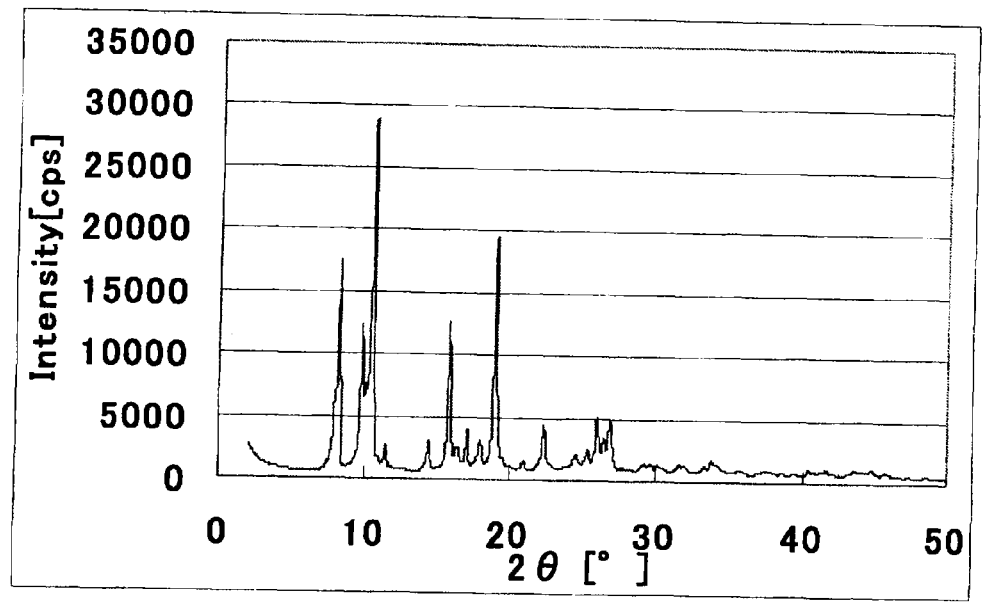
[FIG. 24] A powder X-ray diffraction pattern of a metal complex obtained in Comparative Synthesis Example 8 after vacuum drying.

Under nitrogen atmosphere, 5.35 g (18 mmol) of zinc nitrate hexahydrate, 0.598 g (3.6 mmol) of terephthalic acid, and 1.51 g (3.6 mmol) of N,N'-di(4-pyridyl)-1,4,5,8-naphthalenetetracarboxydiimide were dissolved in 1800 mL of N,N-dimethylformamide at capacity ratio. The mixture was stirred at 353 K for 72 hours. After collecting the precipitated metal complex by suction filtration, the metal complex was washed three times with methanol. Subsequently, the metal complex was dried for 8 hours at 373 K, 50 Pa, thereby obtaining 0.648 g of the target metal complex (yield=41%). The powder X-ray diffraction pattern of the metal complex thus obtained is shown in FIG. 24.

Example 1

Figure 25:
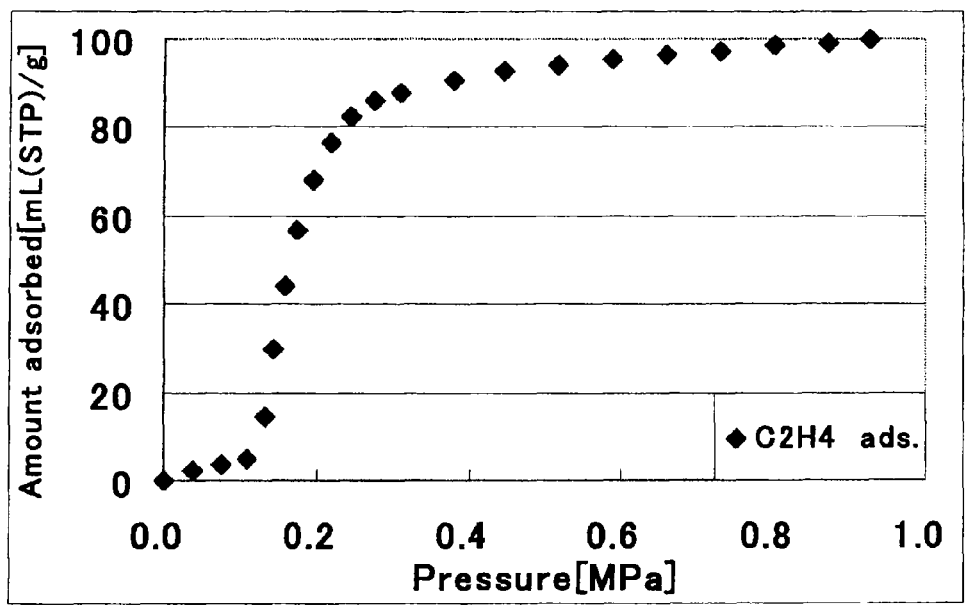
[FIG. 25] A result of adsorption isotherm measurement according to the volumetric method for ethylene at 273 K, for the metal complex obtained in Synthesis Example 2.

FIG. 25 shows a result of adsorption isotherm measurement according to the volumetric method for ethylene at 273 K, for the metal complex obtained in Synthesis Example 2.

Comparative Example 1

Figure 26:
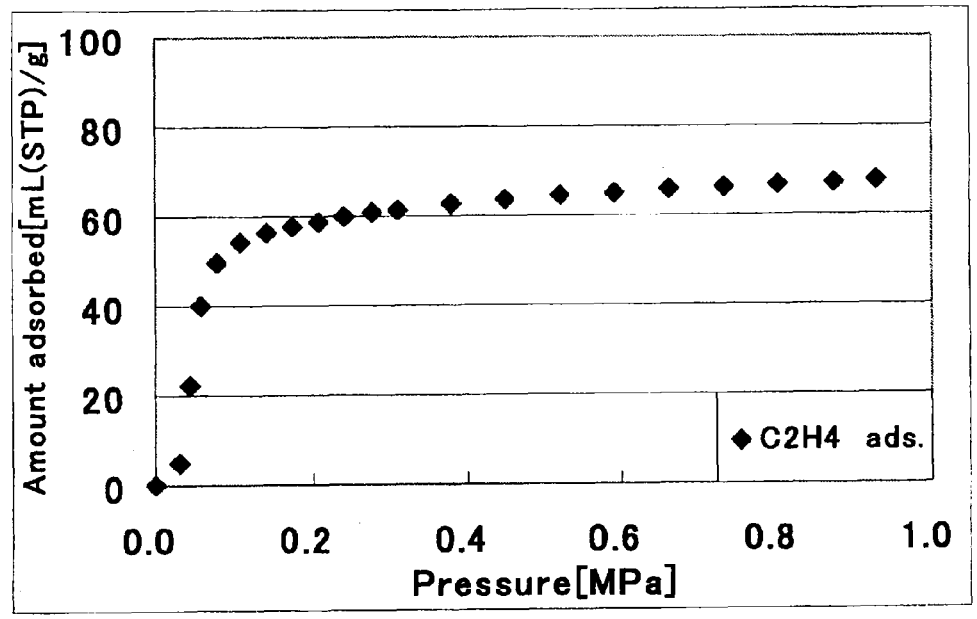
[FIG. 26] A result of adsorption isotherm measurement according to the volumetric method for ethylene at 273 K, for the metal complex obtained in Comparative Synthesis Example 1.

FIG. 26 shows a result of adsorption isotherm measurement according to the volumetric method for ethylene at 273 K, for the metal complex obtained in Synthesis Example 1.

The comparison between FIG. 25 and FIG. 26 confirmed a large ethylene adsorption amount of the metal complex of the present invention. It is thus evident that the metal complex of the present invention is superior as an ethylene adsorbent material.

Example 2

Figure 27:
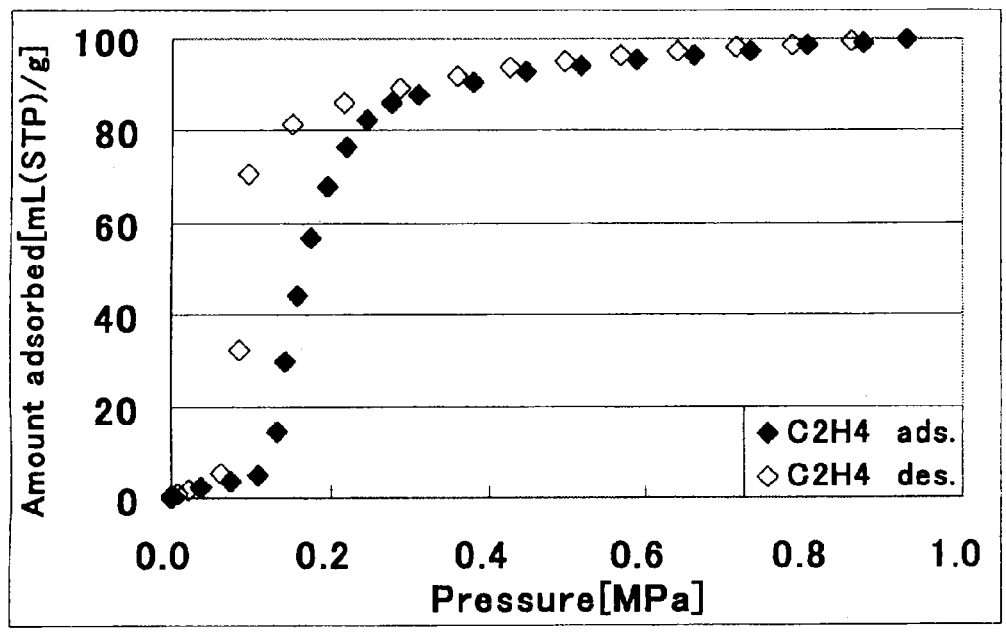
[FIG. 27] A result of absorption/desorption isotherm measurement according to the volumetric method for ethylene at 273 K, for the metal complex obtained in Synthesis Example 2.

FIG. 27 shows a result of adsorption/desorption isotherm measurement according to the volumetric method for ethylene at 273 K, for the metal complex obtained in Synthesis Example 2.

Comparative Example 2

Figure 28:
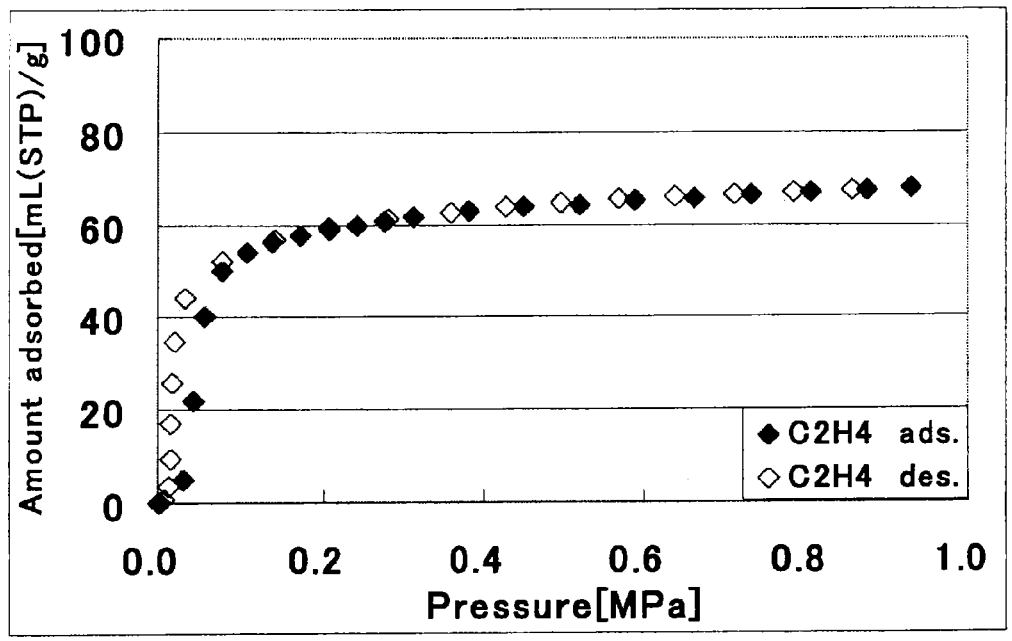
[FIG. 28] A result of absorption/desorption isotherm measurement according to the volumetric method for ethylene at 273 K, for the metal complex obtained in Comparative Synthesis Example 1.

FIG. 28 shows a result of adsorption/desorption isotherm measurement according to the volumetric method for ethylene at 273 K, for the metal complex obtained in Comparative Synthesis Example 1.

The comparison between FIG. 27 and FIG. 28 confirmed a large effective ethylene storage amount of the metal complex of the present invention in a region at a pressure of 0.1 MPa or more, thereby allowing retrieval of the adsorbed ethylene at 0.1 MPa (ordinary pressure); therefore, it is not necessary to decrease the pressure to 0.1 MPa or less. It is thus evident that the metal complex of the present invention is superior as an ethylene storage material.

Example 3

Figure 29:
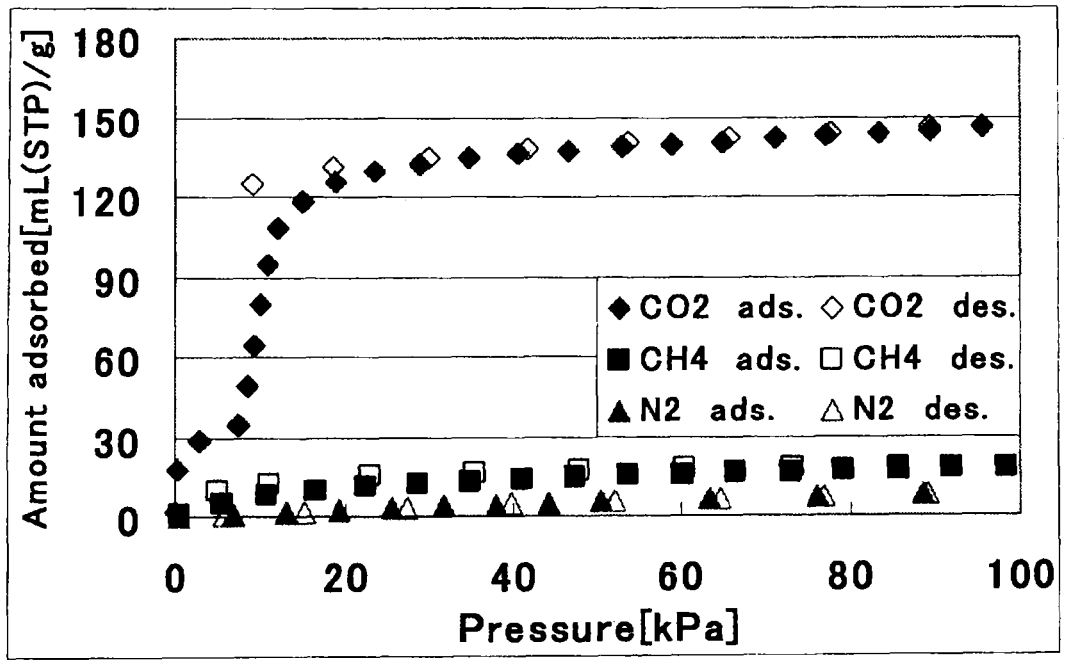
[FIG. 29] A result of absorption/desorption isotherm measurement according to the volumetric method for carbon dioxide, methane, and nitrogen at 195 K, for the metal complex obtained in Synthesis Example 1.

FIG. 29 shows a result of adsorption/desorption isotherm measurement according to the volumetric method for carbon dioxide and methane at 195 K, for the metal complex obtained in Synthesis Example 1. Further, Table 1 shows adsorption amount ratios of carbon dioxide and methane ($CO_2/CH_4$ ratio) at 20, 50, and 90 kPa.

Example 4

FIG. 29 shows a result of adsorption/desorption isotherm measurement according to the volumetric method for carbon dioxide and nitrogen at 195 K, for the metal complex obtained in Synthesis Example 1. Further, Table 2 shows adsorption amount ratios of carbon dioxide and nitrogen ($CO_2/N_2$ ratio) at 20, 50, and 90 kPa.

Example 5

Figure 30:
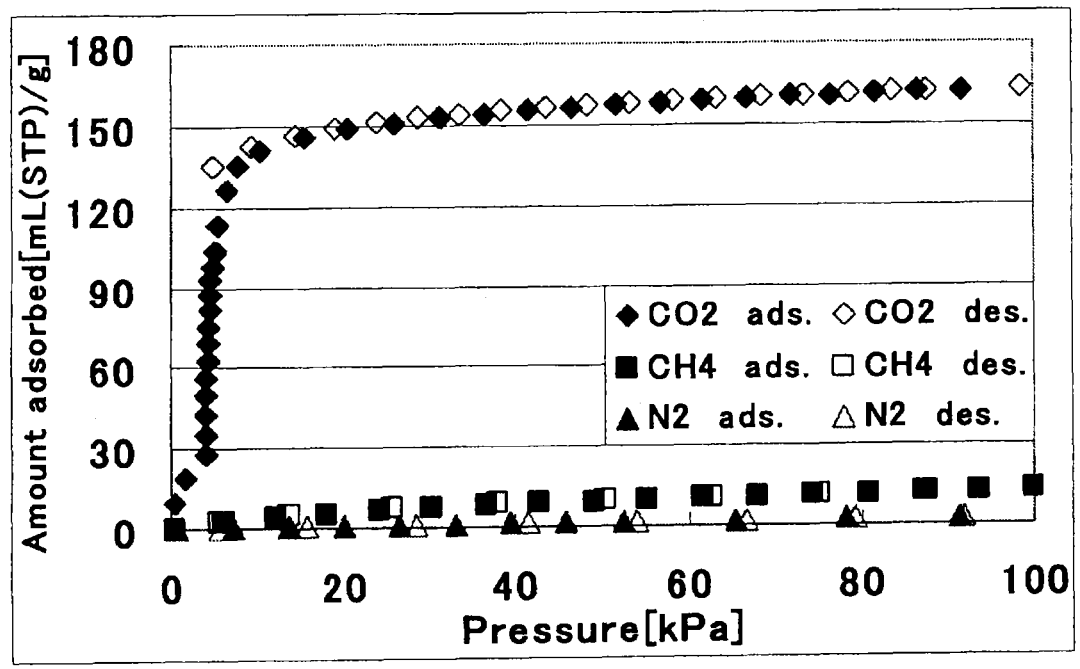
[FIG. 30] A result of absorption/desorption isotherm measurement according to the volumetric method for carbon dioxide, methane, and nitrogen at 195 K, for the metal complex obtained in Synthesis Example 2.

FIG. 30 shows a result of adsorption/desorption isotherm measurement according to the volumetric method for carbon dioxide and methane at 195 K, for the metal complex obtained in Synthesis Example 2. Further, Table 1 shows adsorption amount ratios of carbon dioxide and methane ($CO_2/CH_4$ ratio) at 20, 50, and 90 kPa.

Example 6

FIG. 30 shows a result of adsorption/desorption isotherm measurement according to the volumetric method for carbon dioxide and nitrogen at 195 K, for the metal complex obtained in Synthesis Example 2. Further, Table 2 shows adsorption amount ratios of carbon dioxide and nitrogen ($CO_2/N_2$ ratio) at 20, 50, and 90 kPa.

Example 7

Figure 31:
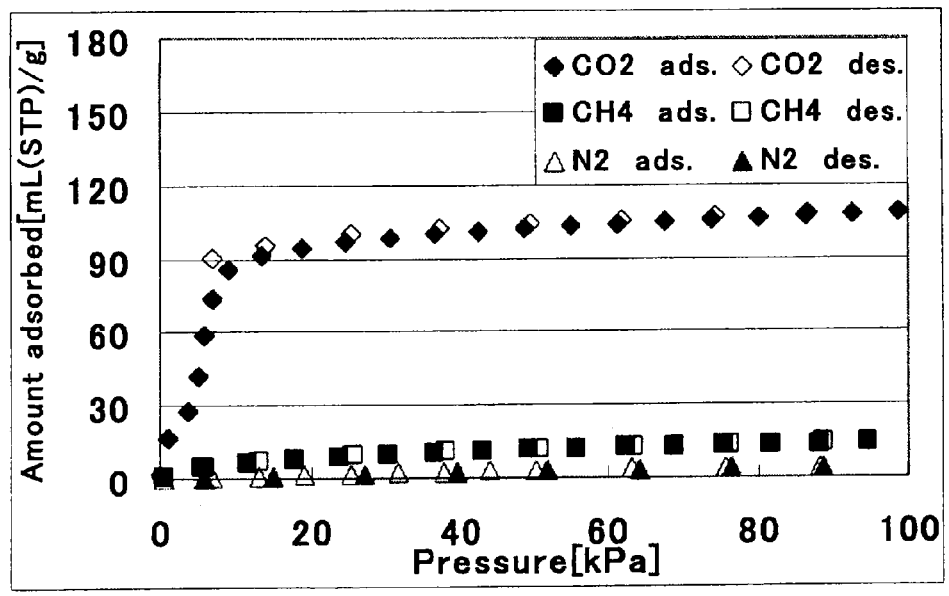
[FIG. 31] A result of absorption/desorption isotherm measurement according to the volumetric method for carbon dioxide, methane, and nitrogen at 195 K, for the metal complex obtained in Synthesis Example 3.

FIG. 31 shows a result of adsorption/desorption isotherm measurement according to the volumetric method for carbon dioxide and methane at 195 K, for the metal complex obtained in Synthesis Example 3. Further, Table 1 shows adsorption amount ratios of carbon dioxide and methane ($CO_2/CH_4$ ratio) at 20, 50, and 90 kPa.

Example 8

FIG. 31 shows a result of adsorption/desorption isotherm measurement according to the volumetric method for carbon dioxide and nitrogen at 195 K, for the metal complex obtained in Synthesis Example 3. Further, Table 2 shows adsorption amount ratios of carbon dioxide and nitrogen ($CO_2/N_2$ ratio) at 20, 50, and 90 kPa.

Comparative Example 3

Figure 32:
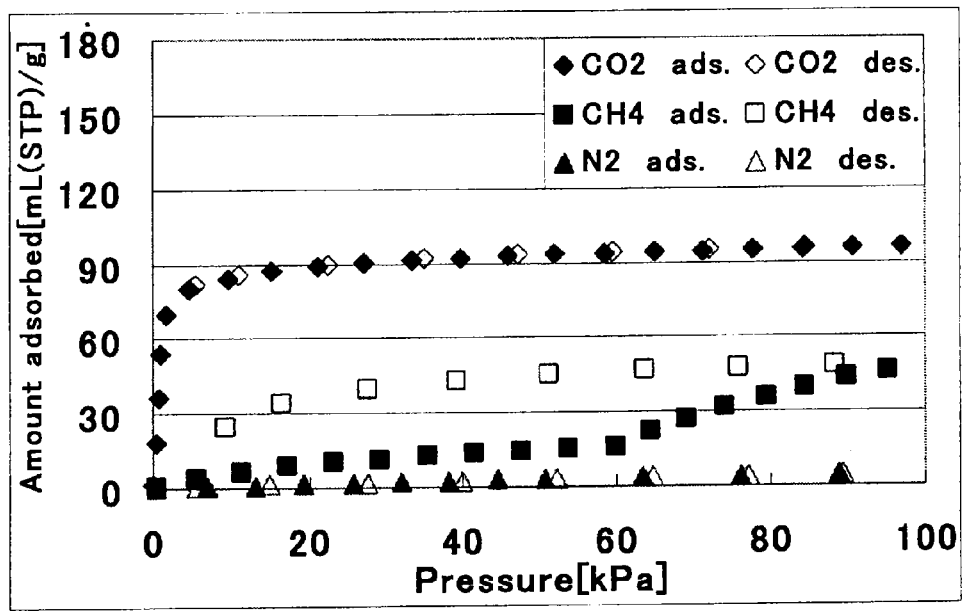
[FIG. 32] A result of absorption/desorption isotherm measurement according to the volumetric method for carbon dioxide, methane, and nitrogen at 195 K, for the metal complex obtained in Comparative Synthesis Example 1.

FIG. 32 shows a result of adsorption/desorption isotherm measurement according to the volumetric method for carbon dioxide and methane at 195 K, for the metal complex obtained in Comparative Synthesis Example 1. Further, Table 1 shows adsorption amount ratios of carbon dioxide and methane ($CO_2/CH_4$ ratio) at 20, 50, and 90 kPa.

Comparative Example 4

FIG. 32 shows a result of adsorption/desorption isotherm measurement according to the volumetric method for carbon dioxide and nitrogen at 195 K, for the metal complex obtained in Comparative Synthesis Example 1. Further, Table 2 shows adsorption amount ratios of carbon dioxide and nitrogen ($CO_2/N_2$ ratio) at 20, 50, and 90 kPa.

Comparative Example 5

Figure 33:
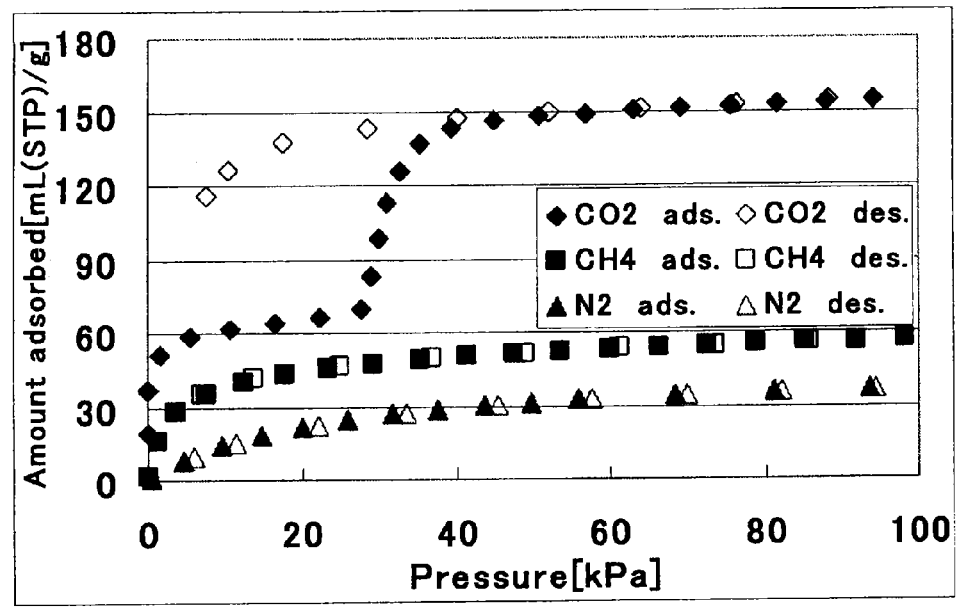
[FIG. 33] A result of absorption/desorption isotherm measurement according to the volumetric method for carbon dioxide, methane, and nitrogen at 195 K, for the metal complex obtained in Comparative Synthesis Example 2.

FIG. 33 shows a result of adsorption/desorption isotherm measurement according to the volumetric method for carbon dioxide and methane at 195 K, for the metal complex obtained in Comparative Synthesis Example 2. Further, Table 1 shows adsorption amount ratios of carbon dioxide and methane ($CO_2/CH_4$ ratio) at 20, 50, and 90 kPa.

Comparative Example 6

FIG. 33 shows a result of adsorption/desorption isotherm measurement according to the volumetric method for carbon dioxide and nitrogen at 195 K, for the metal complex obtained in Comparative Synthesis Example 2. Further, Table 2 shows adsorption amount ratio of carbon dioxide and nitrogen ($CO_2/N_2$ ratio) at 20, 50, and 90 kPa.

TABLE 1

| | Pressure [kPa] | $CO_2$ Amount adsorbed [mL/g] | $CH_4$ Amount adsorbed [mL/g] | $CO_2/CH_4$ ratio |
|---|---|---|---|---|
| Example 3 | 20 | 127 | 11 | 12 |
| | 50 | 139 | 15 | 9 |
| | 90 | 146 | 18 | 8 |

TABLE 1-continued

| | Pressure [kPa] | $CO_2$ Amount adsorbed [mL/g] | $CH_4$ Amount adsorbed [mL/g] | $CO_2/CH_4$ ratio |
|---|---|---|---|---|
| Example 5 | 20 | 149 | 5.5 | 27 |
| | 50 | 157 | 9.3 | 17 |
| | 90 | 162 | 12 | 14 |
| Example 7 | 20 | 95 | 8.3 | 11 |
| | 50 | 104 | 12 | 9 |
| | 90 | 108 | 14 | 8 |
| Comparative Example 3 | 20 | 88 | 9.2 | 10 |
| | 50 | 93 | 15 | 6 |
| | 90 | 96 | 43 | 2 |
| Comparative Example 5 | 20 | 65 | 45 | 1 |
| | 50 | 148 | 52 | 3 |
| | 90 | 154 | 56 | 3 |

Table 1 revealed that the metal complex of the present invention ensures a high carbon dioxide selective adsorption performance and a high carbon dioxide adsorption amount. It is thus evident that the metal complex of the present invention is superior as a separation material for separating carbon dioxide and methane.

TABLE 2

| | Pressure [kPa] | $CO_2$ Amount adsorbed [mL/g] | $N_2$ Amount adsorbed [mL/g] | $CO_2/N_2$ ratio |
|---|---|---|---|---|
| Example 4 | 20 | 127 | 2.5 | 51 |
| | 50 | 139 | 5.5 | 25 |
| | 90 | 146 | 8.1 | 18 |
| Example 6 | 20 | 149 | 0.8 | 186 |
| | 50 | 157 | 1.5 | 105 |
| | 90 | 162 | 2.2 | 74 |
| Example 8 | 20 | 95 | 1.6 | 59 |
| | 50 | 104 | 3.1 | 34 |
| | 90 | 108 | 4.3 | 25 |
| Comparative Example 4 | 20 | 88 | 1.4 | 63 |
| | 50 | 93 | 3.1 | 30 |
| | 90 | 96 | 4.5 | 21 |
| Comparative Example 6 | 20 | 65 | 22 | 3 |
| | 50 | 148 | 32 | 5 |
| | 90 | 154 | 37 | 4 |

Table 2 revealed that the metal complex of the present invention ensures a high carbon dioxide selective adsorption performance and a high carbon dioxide adsorption amount. It is thus evident that the metal complex of the present invention is superior as a separation material for separating carbon dioxide and nitrogen.

Example 9

Figure 34:
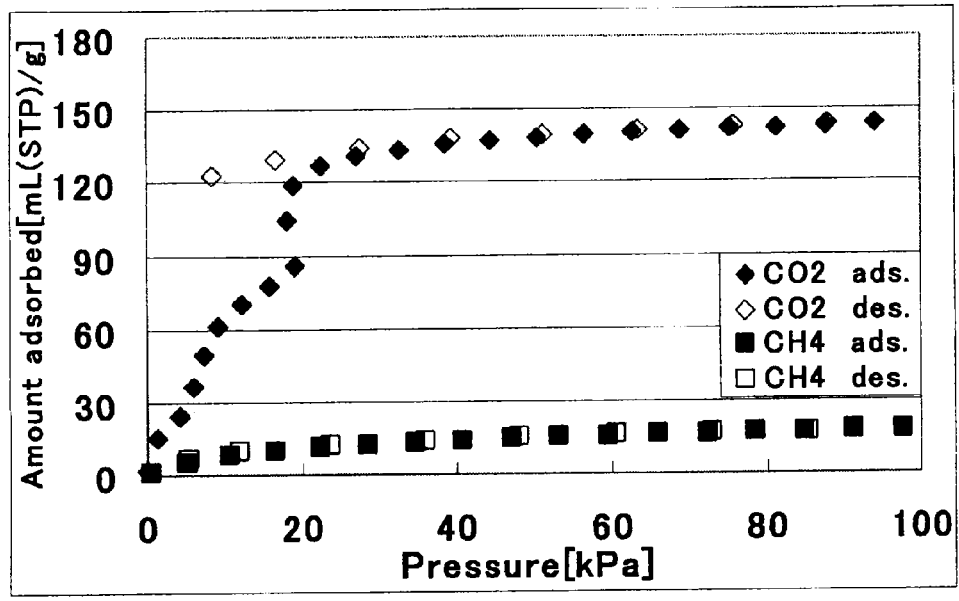
[FIG. 34] A result of absorption/desorption isotherm measurement according to the volumetric method for carbon dioxide and methane at 195 K, for the metal complex obtained in Synthesis Example 4.

FIG. 34 shows a result of adsorption/desorption isotherm measurement according to the volumetric method for carbon dioxide and methane at 195 K, for the metal complex obtained in Synthesis Example 4. Further, Table 3 shows adsorption amount ratios of carbon dioxide and methane ($CO_2/CH_4$ ratio) at 20, 50, and 90 kPa.

Comparative Example 7

Figure 35:
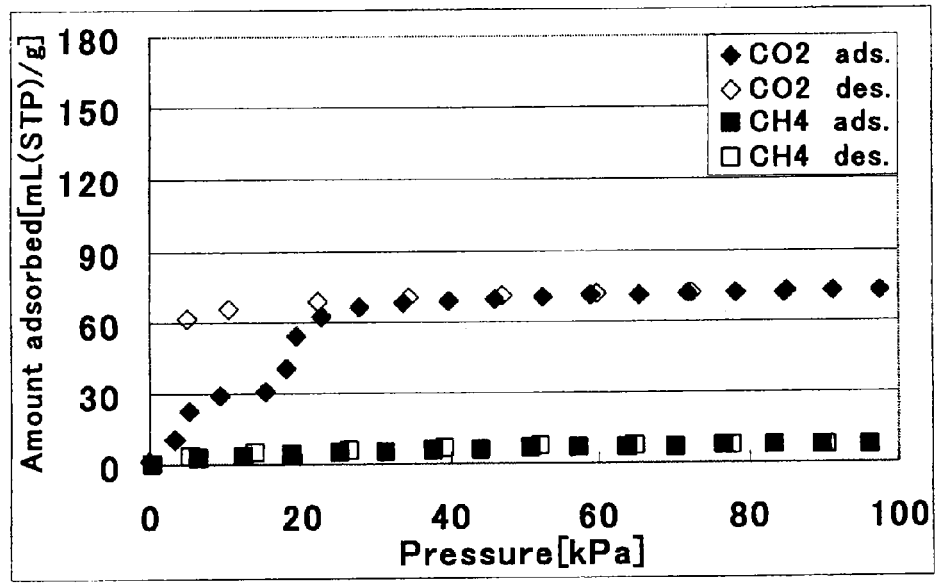
[FIG. 35] A result of absorption/desorption isotherm measurement according to the volumetric method for carbon dioxide and methane at 195 K, for the metal complex obtained in Comparative Synthesis Example 3.

FIG. 35 shows a result of adsorption/desorption isotherm measurement according to the volumetric method for carbon dioxide and methane at 195 K, for the metal complex obtained in Comparative Synthesis Example 3. Further, Table 3 shows adsorption amount ratios of carbon dioxide and methane ($CO_2/CH_4$ ratio) at 20, 50, and 90 kPa.

Comparative Example 8

Figure 36:
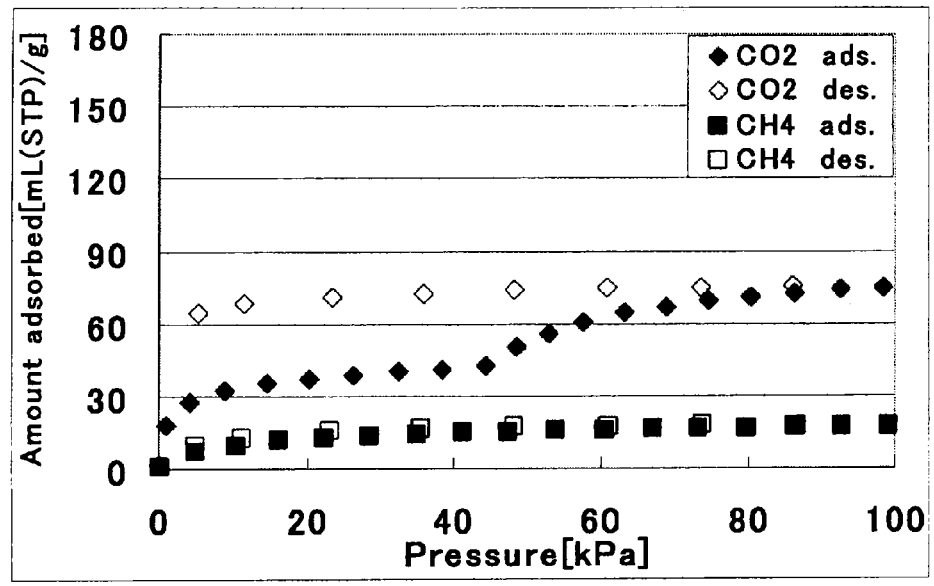
[FIG. 36] A result of absorption/desorption isotherm measurement according to the volumetric method of carbon dioxide and methane at 195 K, for the metal complex obtained in Comparative Synthesis Example 4.

FIG. 36 shows a result of adsorption/desorption isotherm measurement according to the volumetric method for carbon dioxide and methane at 195 K, for the metal complex obtained in Comparative Synthesis Example 4. Further, Table 3 shows an adsorption amount ratio of carbon dioxide and methane ($CO_2/CH_4$ ratio) at 20, 50, and 90 kPa.

Comparative Example 9

Figure 37:
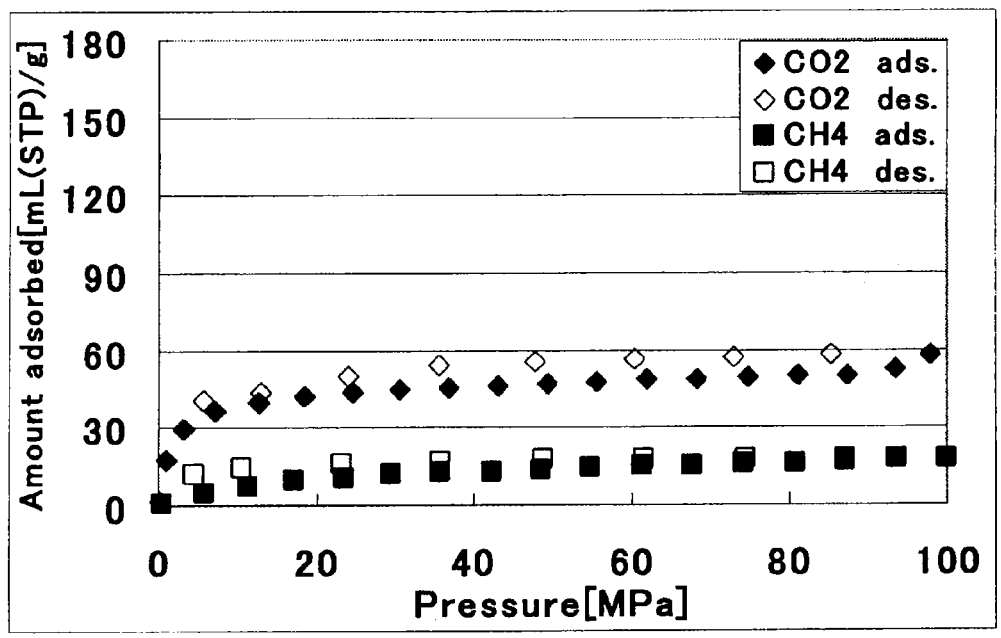
[FIG. 37] A result of absorption/desorption isotherm measurement according to the volumetric method for carbon dioxide and methane at 195 K, for the metal complex obtained in Comparative Synthesis Example 5.

FIG. 37 shows a result of adsorption/desorption isotherm measurement according to the volumetric method for carbon dioxide and methane at 195 K, for the metal complex obtained in Comparative Synthesis Example 5. Further, Table 3 shows adsorption amount ratios of carbon dioxide and methane ($CO_2/CH_4$ ratio) at 20, 50, and 90 kPa.

TABLE 3

| | Pressure [kPa] | $CO_2$ Amount adsorbed [mL/g] | $CH_4$ Amount adsorbed [mL/g] | $CO_2/CH_4$ ratio |
|---|---|---|---|---|
| Example 9 | 20 | 122 | 10 | 12 |
| | 50 | 138 | 15 | 9 |
| | 90 | 143 | 17 | 8 |
| Comparative Example 7 | 20 | 40 | 4.2 | 10 |
| | 50 | 70 | 6.1 | 11 |
| | 90 | 72 | 7.6 | 9 |
| Comparative Example 8 | 20 | 37 | 12 | 3 |
| | 50 | 50 | 15 | 3 |
| | 90 | 73 | 18 | 4 |
| Comparative Example 9 | 20 | 42 | 10 | 4 |
| | 50 | 47 | 14 | 3 |
| | 90 | 52 | 17 | 3 |

Table 3 revealed that the metal complex of the present invention ensures a high carbon dioxide selective adsorption performance and a high carbon dioxide adsorption amount. It is thus evident that the metal complex of the present invention is superior as a separation material for separating carbon dioxide and methane.

Example 10

Figure 38:
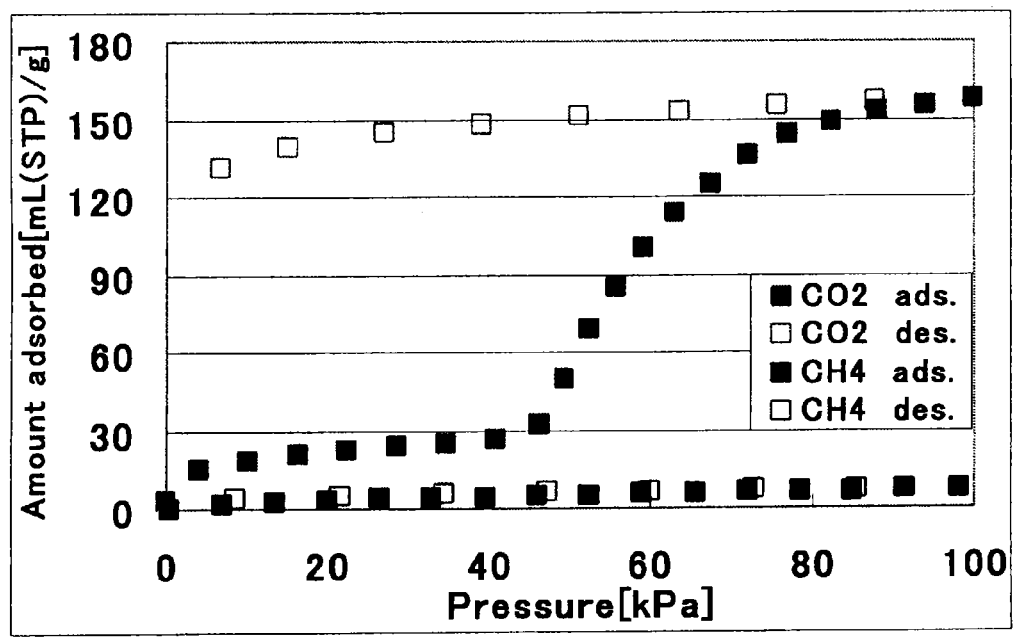
[FIG. 38] A result of absorption/desorption isotherm measurement according to the volumetric method for carbon dioxide and methane at 195 K, for the metal complex obtained in Synthesis Example 5.

FIG. 38 shows a result of adsorption/desorption isotherm measurement according to the volumetric method for carbon dioxide and methane at 195 K, for the metal complex obtained in Synthesis Example 5. Further, Table 3 shows adsorption amount ratios of carbon dioxide and methane ($CO_2/CH_4$ ratio) at 20, 50, and 90 kPa.

Example 11

Figure 39:
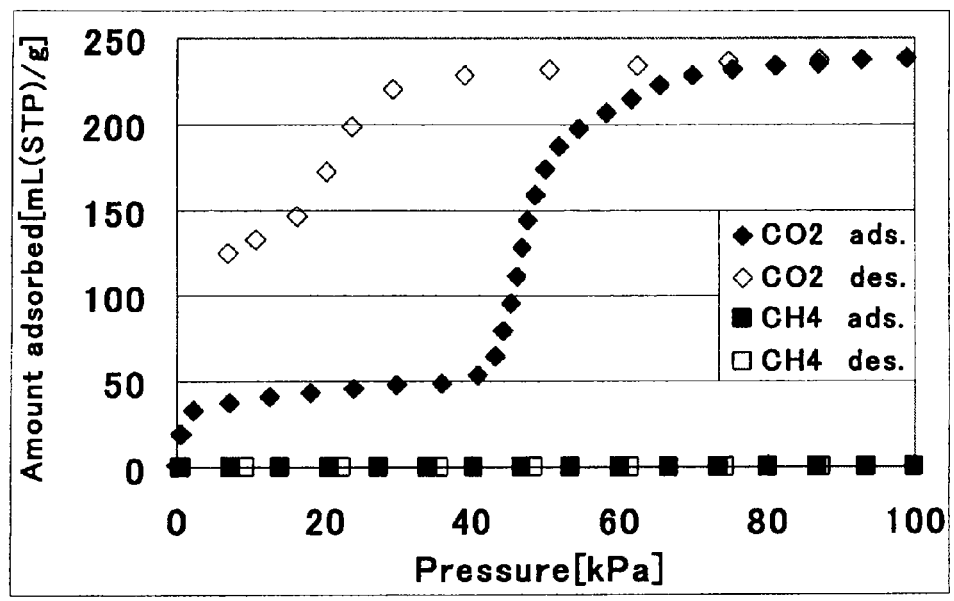
[FIG. 39] A result of absorption/desorption isotherm measurement according to the volumetric method for carbon dioxide and methane at 195 K, for the metal complex obtained in Synthesis Example 6.

FIG. 39 shows a result of adsorption/desorption isotherm measurement according to the volumetric method for carbon dioxide and methane at 195 K, for the metal complex obtained in Synthesis Example 6. Further, Table 3 shows adsorption amount ratios of carbon dioxide and methane ($CO_2/CH_4$ ratio) at 20, 50, and 90 kPa.

Comparative Example 10

Figure 40:
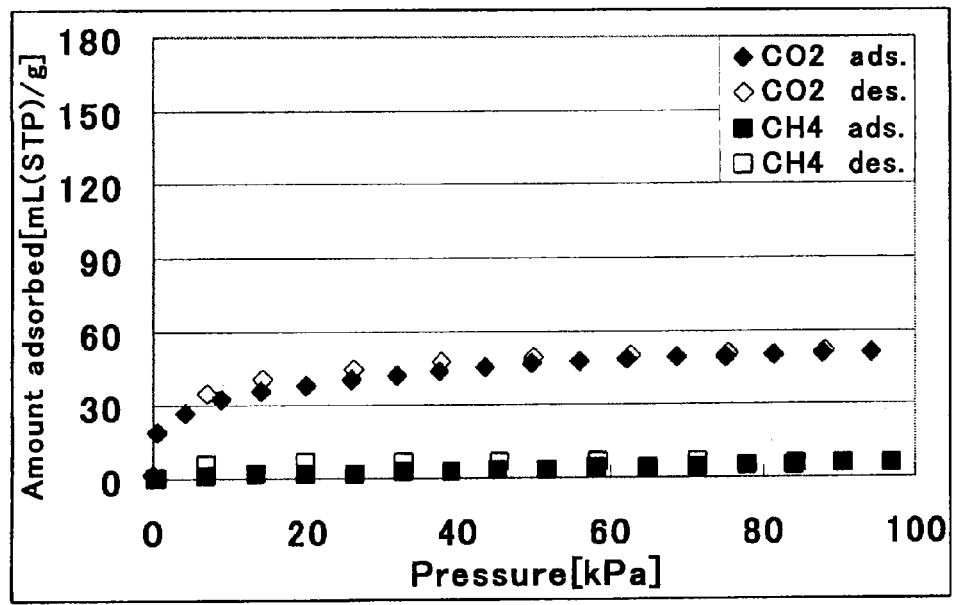
[FIG. 40] A result of absorption/desorption isotherm measurement according to the volumetric method for carbon dioxide and methane at 195 K, for the metal complex obtained in Comparative Synthesis Example 6.

FIG. 40 shows a result of adsorption/desorption isotherm measurement according to the volumetric method for carbon dioxide and methane at 195 K, for the metal complex obtained in Comparative Synthesis Example 6. Further, Table 3 shows adsorption amount ratios of carbon dioxide and methane ($CO_2/CH_4$ ratio) at 20, 50, and 90 kPa.

Comparative Example 11

Figure 41:
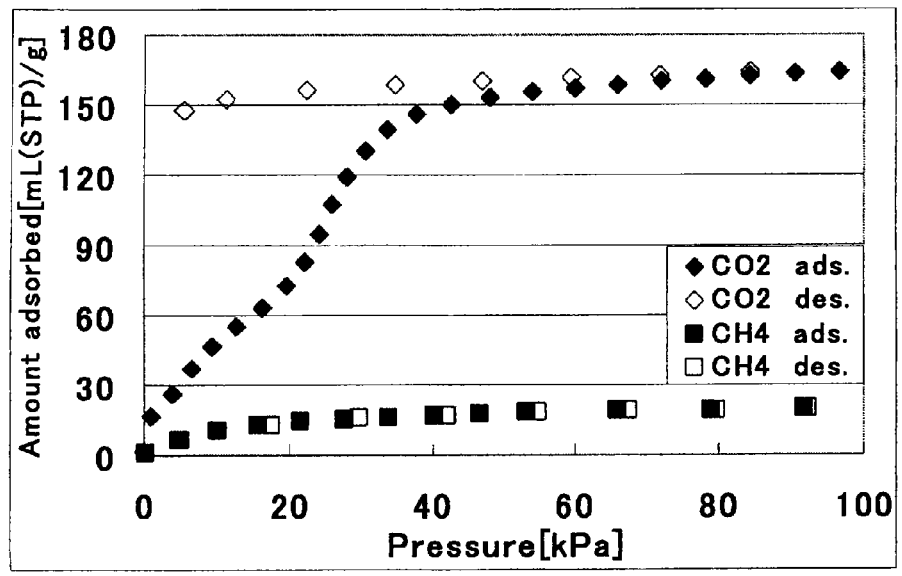
[FIG. 41] A result of absorption/desorption isotherm measurement according to the volumetric method for carbon dioxide and methane at 195 K, for the metal complex obtained in Comparative Synthesis Example 7.

FIG. 41 shows a result of adsorption/desorption isotherm measurement according to the volumetric method for carbon dioxide and methane at 195 K, for the metal complex obtained in Comparative Synthesis Example 7. Further, Table 3 shows adsorption amount ratios of carbon dioxide and methane ($CO_2/CH_4$ ratio) at 20, 50, and 90 kPa.

Comparative Example 12

Figure 42:
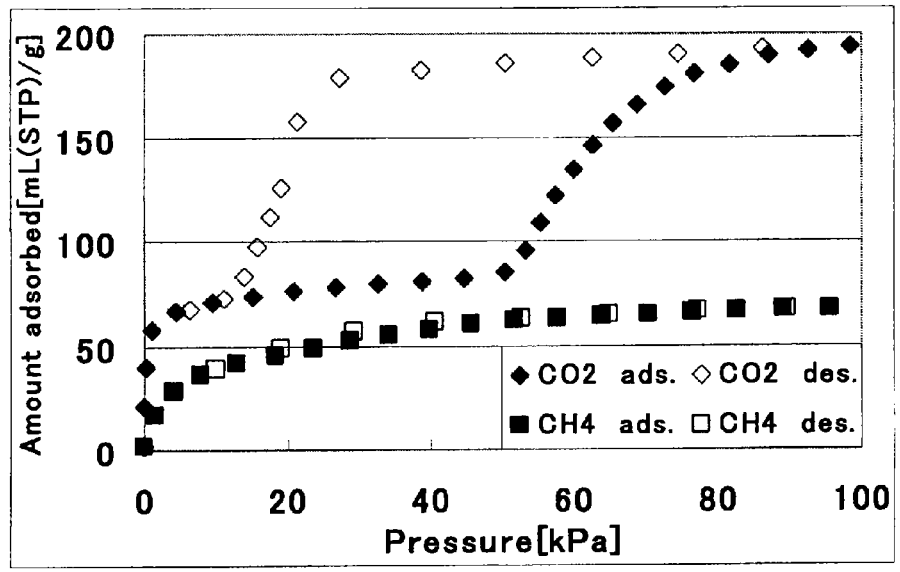
[FIG. 42] A result of absorption/desorption isotherm measurement according to the volumetric method for carbon dioxide and methane at 195 K, for the metal complex obtained in Comparative Synthesis Example 8.

FIG. 42 shows a result of adsorption/desorption isotherm measurement according to the volumetric method for carbon dioxide and methane at 195 K, for the metal complex obtained in Comparative Synthesis Example 8. Further, Table 3 shows adsorption amount ratios of carbon dioxide and methane ($CO_2/CH_4$ ratio) at 20, 50, and 90 kPa.

TABLE 4

|  | Pressure [kPa] | $CO_2$ Amount adsorbed [mL/g] | $CH_4$ Amount adsorbed [mL/g] | $CO_2/CH_4$ ratio |
|---|---|---|---|---|
| Example 10 | 20 | 21 | 3.0 | 7 |
|  | 50 | 50 | 4.9 | 10 |
|  | 90 | 154 | 5.0 | 31 |
| Example 11 | 20 | 44 | 0.1 | 440 |
|  | 50 | 174 | 0.2 | 870 |
|  | 90 | 237 | 0.2 | 1185 |
| Comparative Example 10 | 20 | 38 | 1.9 | 20 |
|  | 50 | 47 | 6.0 | 8 |
|  | 90 | 51 | 6.0 | 9 |
| Comparative Example 11 | 20 | 72 | 13 | 6 |
|  | 50 | 154 | 18 | 9 |
|  | 90 | 163 | 20 | 8 |
| Comparative Example 12 | 20 | 75 | 45 | 2 |
|  | 50 | 85 | 61 | 1 |
|  | 90 | 189 | 67 | 3 |

The comparison in Table 4 revealed that the metal complex of the present invention ensures a high carbon dioxide selective adsorption performance and a high carbon dioxide adsorption amount. It is thus evident that the metal complex of the present invention is superior as a separation material for separating methane and carbon dioxide.

Example 12

Figure 43:
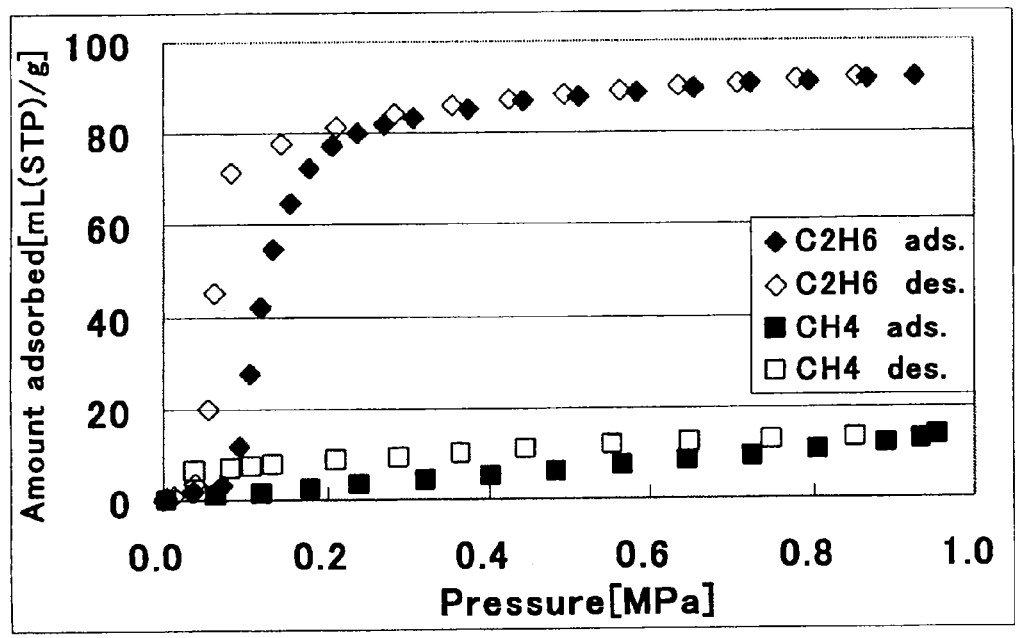
[FIG. 43] A result of adsorption/desorption isotherm measurement according to the volumetric method for ethane and methane at 273 K, for the metal complex obtained in Synthesis Example 2.

FIG. 43 shows a result of adsorption isotherm measurement according to the volumetric method for ethane and methane at 273 K, for the metal complex obtained in Synthesis Example 2. Further, Table 5 shows adsorption amount ratios of ethane and methane ($C_2H_6/CH_4$ ratio) at 0.2, 0.5, and 0.9 MPa.

Comparative Example 13

Figure 44:
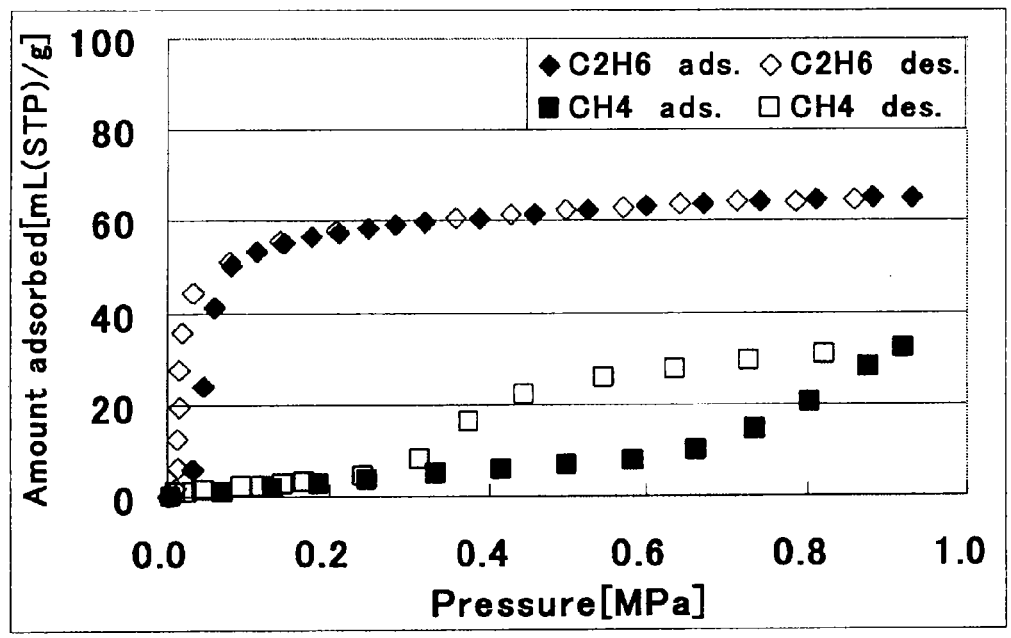
[FIG. 44] A result of adsorption/desorption isotherm measurement according to the volumetric method for ethane and methane at 273 K, for the metal complex obtained in Comparative Synthesis Example 1.

FIG. 44 shows a result of adsorption isotherm measurement according to the volumetric method for ethane and methane at 273 K, for the metal complex obtained in Comparative Synthesis Example 1. Further, Table 5 shows adsorption amount ratios of ethane and methane ($C_2H_6/CH_4$ ratio) at 0.2, 0.5, and 0.9 MPa.

TABLE 5

|  | Pressure [MPa] | $C_2H_6$ Amount adsorbed [mL/g] | $CH_4$ Amount adsorbed [mL/g] | $C_2H_6/CH_4$ ratio |
|---|---|---|---|---|
| Example 12 | 0.2 | 78 | 2.5 | 31 |
|  | 0.5 | 88 | 6.0 | 15 |
|  | 0.9 | 92 | 12 | 8 |
| Comparative Example 13 | 0.2 | 58 | 2.9 | 20 |
|  | 0.5 | 62 | 7.0 | 9 |
|  | 0.9 | 65 | 32 | 2 |

The comparison in Table 5 revealed that the metal complex of the present invention ensures a high ethane selective adsorption performance and a high ethane adsorption amount. It is thus evident that the metal complex of the present invention is superior as a separation material for separating ethane and methane.

Example 13

Figure 45:
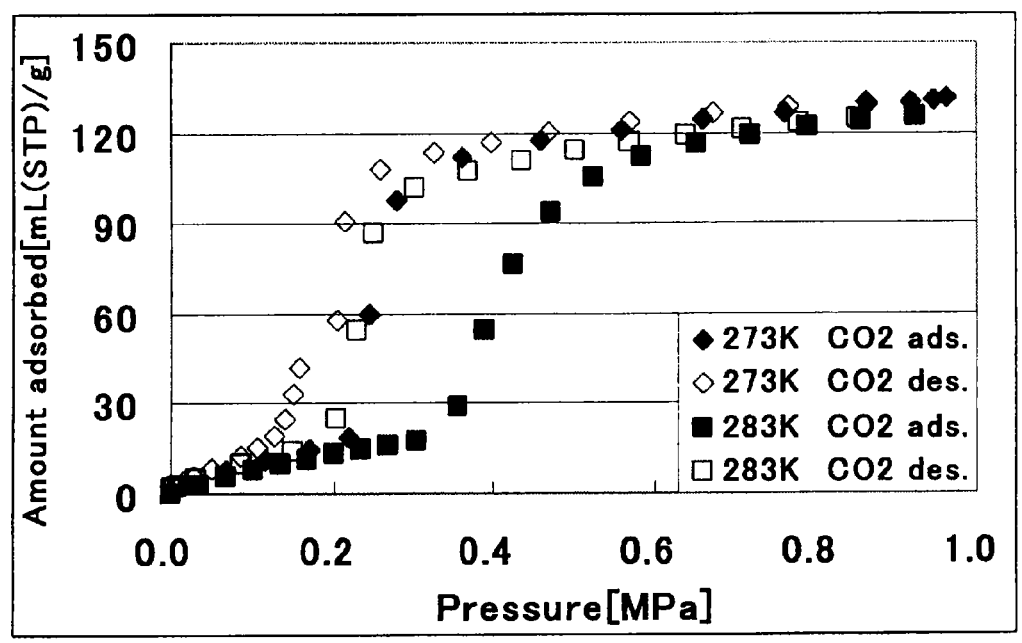
[FIG. 45] A result of absorption/desorption isotherm measurement according to the volumetric method for carbon dioxide at 273 K and 283 K, for the metal complex obtained in Synthesis Example 2.

Adsorption/desorption isotherm measurement was performed according to the volumetric method for carbon dioxide at 273 K and 283 K of the metal complex obtained in Synthesis Example 2. FIG. 45 shows the result.

FIG. 45 revealed that the adsorption starting pressure of the metal complex of the present invention is temperature-dependent and controllable. Owing to this characteristic, it is possible to improve the separation extent in the temperature swing adsorption process, compared with the case using a hitherto known separation material.

The invention claimed is:

1. A metal complex, comprising:
(I) a dicarboxylic acid compound of Formula (I):

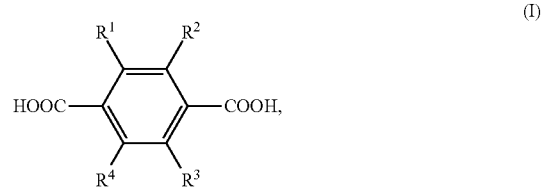

wherein $R^1$, $R^2$, $R^3$, and $R^4$ are the same or different, and are each independently a hydrogen atom, an alkyl group optionally comprising a substituent, an alkoxy group, a formyl group, an acyloxy group, an alkoxycarbonyl group, a nitro group, a cyano group, an amino group, a monoalkyl amino group, a dialkyl amino group, a acylamino group or a halogen atom; or $R^1$ and $R^2$, or $R^3$ and $R^4$ together optionally form an alkylene group or an alkenylene group optionally comprising a substituent;
(II) at least one metal ion selected from the group consisting of ions of a metal belonging to Group 2 and Groups 7 to 12 of the periodic table; and
(III) an organic ligand comprising 2 to 7 heteroatoms, wherein the organic ligand is capable of bidentate binding to the metal ion, the organic ligand belongs to the $D_{\infty h}$ point group, and the organic ligand has a longitudinal length of not less than 8.0 Å and less than 16.0 Å.

2. The metal complex of claim 1, wherein the dicarboxylic acid compound (I) is terephthalic acid, 2-methoxyterephthalic acid, 2-nitroterephthalic acid, or any mixture thereof.

3. The metal complex of claim 1, wherein the organic ligand (III) is 1,2-bis(4-pyridyl)ethyne, 1,4-bis(4-pyridyl)

benzene, 3,6-di(4pyridyl)-1,2,4,5-tetrazine, 4,4'-bis(4-pyridyl)biphenyl, or any mixture thereof.

4. The metal complex of claim 1, wherein the metal ion is a zinc ion.

5. An adsorbent material, comprising the metal complex claim 1.

6. The adsorbent material of claim 5, wherein the adsorbent material absorbs carbon dioxide, hydrogen, carbon monoxide, oxygen, nitrogen, a hydrocarbon comprising 1 to 4 carbon atoms, a noble gas, hydrogen sulfide, ammonia, sulfur oxides, a nitrogen oxide, a siloxane, water vapor, or organic vapor.

7. A storage materiah comprising the metal complex of claim 1.

8. The storage material of claim 7, wherein the storage material stores carbon dioxide, hydrogen, carbon monoxide, oxygen, nitrogen, a hydrocarbon comprising 1 to 4 carbon atoms, a noble gas, hydrogen sulfide, ammonia, water vapor, or organic vapor.

9. A separation material, comprising the metal complex of claim 1.

10. The separation material of claim 9, wherein the separation material separates carbon dioxide, hydrogen, carbon monoxide, oxygen, nitrogen, a hydrocarbon comprising 1 to 4 carbon atoms, a noble gas, hydrogen sulfide, ammonia, a sulfur oxide, a nitrogen oxide, a siloxane, water vapor, or organic vapor from a gas mixture.

11. The separation material of claim 9, wherein the separation material separates carbon dioxide from methane, carbon dioxide from hydrogen, carbon dioxide from nitrogen, ethane from methane, or methane from air.

12. A method for producing the metal complex of claim 1, the method comprising:
reacting, in a solvent, the dicarboxylic acid compound of formula (I), at least one metal salt selected from the groups consisting of a salt of a metal belonging to Group 2 and Groups 7 to 12 of the periodic table, and the organic ligand (III), thereby precipitating the metal complex.

13. A process for adsorbing a gas, the process comprising:
(I) contacting a gas with the adsorption material of claim 5, thereby adsorbing the gas to the adsorption material,
wherein the gas is carbon dioxide, hydrogen, carbon monoxide, oxygen, nitrogen, a hydrocarbon comprising 1 to 4 carbon atoms, a noble gas, hydrogen sulfide, ammonia, a sulfur oxide, a nitrogen oxide, a siloxane, water vapor, or an organic vapor.

14. A process for storing a gas, the process comprising:
(I) contacting a gas with the storage material of claim 7 with a gas at an adsorption pressure and an adsorption temperature, thereby adsorbing the gas to the storage material; and then
(II) reducing the pressure to a desorption pressure or increasing the temperature to a desorption temperature, thereby desorbing the gas from the storage material,
wherein the gas is carbon dioxide, hydrogen, carbon monoxide, oxygen, nitrogen, a hydrocarbon comprising 1 to 4 carbon atoms, a noble gas, hydrogen sulfide, ammonia, a sulfur oxide, a nitrogen oxide, a siloxane, water vapor, or an organic vapor.

15. A process for separating a gas from a gas mixture, the process comprising:
(I) contacting a gas mixture comprising a first gas and a second gas with the separation material of claim 9, to selectively adsorb the first gas to the storage material,
wherein the gas mixture comprises as the first gas and the second gas, respectively, carbon dioxide and methane, carbon dioxide and hydrogen, carbon dioxide and nitrogen, ethane and methane, or methane and air.

16. The metal complex of claim 4, wherein the dicarboxylic acid compound (I) is 2-nitroterephthalic acid and the organic ligand is 1,4-bis(4-pyridyl)benzene.

17. The metal complex of claim 4, wherein the dicarboxylic acid compound (I) is 2-nitroterephthalic acid and the organic ligand is 1,2-bis(4-pyridyl)ethyne.

18. The metal complex of claim 4, wherein the dicarboxylic acid compound (I) is 2-nitroterephthalic acid and the organic ligand is 4,4'-bis(4-pyridyl)biphenyl.

19. The metal complex of claim 4, wherein the dicarboxylic acid compound (I) is 2-methoxyterephthalic acid and the organic ligand is 1,2-bis(4-pyridyl)ethyne.

20. The metal complex of claim 4, wherein the dicarboxylic acid compound (I) is terephthalic acid and the organic ligand is 1,2-bis(4-pyridyl)ethyne.

* * * * *